(12) United States Patent
Mandge et al.

(10) Patent No.: US 12,213,972 B2
(45) Date of Patent: Feb. 4, 2025

(54) STABLE PHARMACEUTICAL COMPOSITIONS OF APIXABAN

(71) Applicant: Slayback Pharma LLC, Princeton, NJ (US)

(72) Inventors: Shailendra Mandge, Hyderabad (IN); Venkateshwar Reddy Keesara, Hyderabad (IN); Harish Gunda, Nizamabad (IN); Naga Venkata Durga Prasad Ketha, Hyderabad (IN); Satheesh Balasubramanian, Hyderabad (IN); Sumitra Ashokkumar Pillai, Hyderabad (IN); Sushant Omprakash Dube, Navi Mumbai (IN); Praveen Kumar Subbappa, Princeton, NJ (US)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

(21) Appl. No.: 18/420,099

(22) Filed: Jan. 23, 2024

(65) Prior Publication Data

US 2024/0197705 A1    Jun. 20, 2024

Related U.S. Application Data

(63) Continuation-in-part of application No. 18/357,295, filed on Jul. 24, 2023, now abandoned.

(30) Foreign Application Priority Data

Jul. 27, 2022  (IN) .............................. 202241043065

(51) Int. Cl.
*A61K 31/444* (2006.01)
*A61K 9/48* (2006.01)

(52) U.S. Cl.
CPC .......... *A61K 31/444* (2013.01); *A61K 9/4825* (2013.01); *A61K 9/4858* (2013.01); *A61K 9/4866* (2013.01); *A61K 9/4891* (2013.01)

(58) Field of Classification Search
CPC .................................................... A61K 31/437
See application file for complete search history.

(56) References Cited

U.S. PATENT DOCUMENTS 5,837,277 A * 11/1998 Hayward ............. A61K 9/5073
424/441

FOREIGN PATENT DOCUMENTS

| WO | WO-03068231 A2 * | 8/2003 | ......... A61K 31/4415 |
| WO | WO-2010147978 A1 * | 12/2010 | ........... A61K 31/437 |
| WO | WO-2012082209 A1 * | 6/2012 | ........... A61K 31/702 |
| WO | WO-2014052678 A1 * | 4/2014 | ........... A61K 31/437 |

* cited by examiner

*Primary Examiner* — Clinton A Brooks
*Assistant Examiner* — George W Kosturko
(74) *Attorney, Agent, or Firm* — Paul E. Dietze; Parker Poe Adams & Bernstein, LLP

(57) ABSTRACT

The present invention relates to stable pharmaceutical compositions comprising apixaban or its pharmaceutically acceptable salts thereof. The present invention further relates to a capsule composition comprising a therapeutically effective amount of apixaban solubilized or dispersed in a pharmaceutically acceptable carrier, wherein the therapeutically effective amount of apixaban ranges from about 0.5 mg/unit dosage form to about 50 mg/unit dosage form. The present invention also provides manufacturing processes thereof and use of the said compositions for prevention, treatment or prophylaxis of disorders in human patients in need thereof.

18 Claims, 1 Drawing Sheet

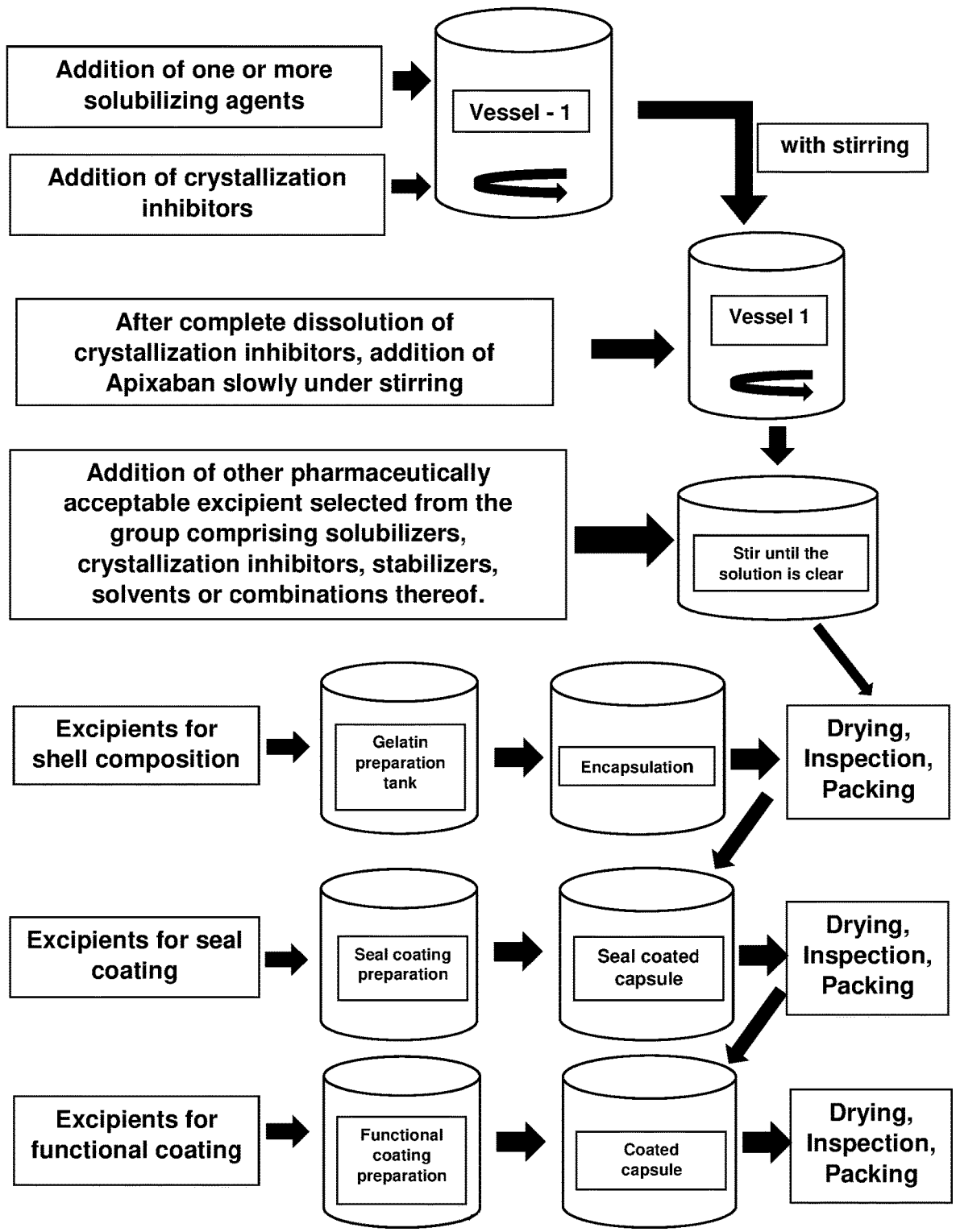

STABLE PHARMACEUTICAL COMPOSITIONS OF APIXABAN

CROSS REFERENCE TO RELATED APPLICATIONS

This application is a continuation-in-part of U.S. application Ser. No. 18/357,295, filed on Jul. 24, 2023, which claims the benefit of Indian Provisional Application No. 202241043065, as filed on Jul. 27, 2022, the entire contents of which are incorporated herein.

FIELD OF THE INVENTION

The present invention relates to stable pharmaceutical compositions comprising apixaban or pharmaceutically acceptable salts thereof. The present invention further relates to capsule compositions comprising a therapeutically effective amount of apixaban dispersed in a pharmaceutically acceptable carrier, wherein the therapeutically effective amount of apixaban ranges from about 0.5 mg/unit dosage form to about 50 mg/unit dosage form. The present invention also provides manufacturing processes thereof and use of the said inventive compositions for prevention, treatment or prophylaxis of disorders in human patients in need thereof.

BACKGROUND OF THE INVENTION

Apixaban is an orally active, selective and highly potent inhibitor of coagulation factor Xa (FXa), that directly and reversibly binds to the active site of FXa, and exerts anticoagulant and antithrombotic effects by diminishing the conversion of prothrombin to thrombin. Apixaban is thereby used as an anticoagulant for prophylaxis and treatment of thromboembolic disorders. Chemically, this compound belongs to the class of phenylpiperidines, described as 1-(4-methoxyphenyl)-7-oxo-6-[4-(2-oxopiperidin-1-yl)phenyl]-4,5-dihydropyrazolo [3,4-c]pyridine-3-carboxamide and is represented by the structural formula (I):

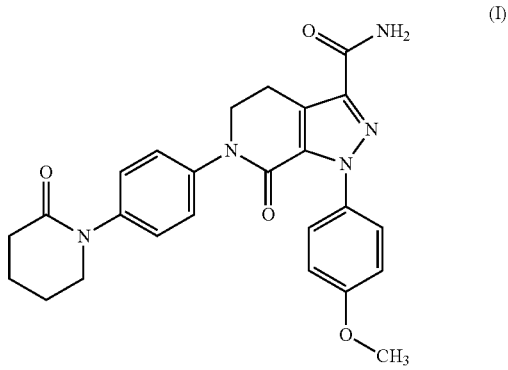 [SMILES: COc1ccc(-n2nc(C(N)=O)c3c2C(=O)N(c2ccc(N4CCCCC4=O)cc2)CC3)cc1]

(I)

Currently, apixaban is marketed in United States under the brand name Eliquis® (apixaban tablets; 2.5 mg and 5 mg; having National Drug Code Number 0003-0893-21, 0003-0893-31, 0003-0894-21, 0003-0894-31, 0003-0894-70, 0003-0894-74, and NDA Number 202155). Eliquis® is known to be effective in adults for reducing the risk of stroke and systemic embolism in patients with nonvalvular atrial fibrillation; for the prophylaxis of deep vein thrombosis (DVT), which may lead to pulmonary embolism (PE), in patients who have undergone hip or knee replacement surgery; and for the treatment of DVT and PE, and for the reduction in the risk of recurrent DVT and PE.

The recommended dose of apixaban ranges from 2.5 mg to 10 mg taken orally twice daily. In the case of treatment of DVT and PE, the recommended dose of apixaban is 10 mg taken orally twice daily for the first 7 days of therapy. After 7 days, the recommended dose is 5 mg taken orally twice daily. This demonstrates that apixaban is a highly potent active pharmaceutical ingredient (API). Due to its very high potency, apixaban invites a lot of formulation issues such as challenges in achieving uniform distribution of the drug (content uniformity), and additional handling restrictions on a large manufacturing scale, especially in a solid dosage form such as tablets.

Furthermore, drugs that have a low solubility in water, and particularly drugs that are practically insoluble in water (for example drugs having a water solubility at 25° C. of about 100 mg/l or less), present challenges to the preparation of pharmaceutical formulations. In particular, achieving an acceptable dissolution rate and oral bioavailability can be difficult. Apixaban, in common with some other direct factor Xa inhibitors, is practically insoluble in water (i.e. 0.04 mg/mL), and moreover has a low solubility in many organic solvents, including ethanol, and hence presents significant challenges to formulators. Additionally, as apixaban exhibits low water solubility, mixture with conventional excipients could prove to be difficult due to issues such as unpredictable dissolution rates, irregular bioavailability, or instability. Accordingly, a suitable and robust pharmaceutical composition which can overcome the above problems is the current need.

Liquid oral formulations, generally provide optimal "content uniformity". However, an unpleasant, strong and bitter taste of active ingredient in such formulations may lead to poor compliance or even non-compliance of the patient towards treatment and thus might have a negative impact on the efficiency of treatment. Although the taste can be masked using excipients such as sweeteners, flavors, or taste masking agents, it is desirable to minimize the use of such additional excipients for formulating oral liquid formulations.

There continues to be a need for developing superior formulations which can solubilize and stabilize apixaban, provide adequate bioavailability, and ultimately deliver the active ingredient to the appropriate target within the human body.

Capsules in particular have gained popularity and acceptance over tablets due to their elegant appearance. Capsules, in general, are easier to swallow, conceal unpleasant odors, and can easily be colored to protect ingredients from light. Specifically, soft gelatin capsules (referred to as liquid gels or soft-gels) are a unique drug delivery system that can provide distinct advantages over traditional dosage forms such as tablets, hard gelatin capsules and liquid oral formulations. The active ingredient exists in liquid form (solubilized or dispersed) in soft-gels which allows rapid release of active ingredient as soon as the gelatin shell ruptures.

U.S. Pat. No. 9,326,945 discloses a solid pharmaceutical composition comprising crystalline apixaban particles having $D_{90}$ particle size equal to or less than about 89 μm. The disclosed compositions require the particle size of apixaban to be controlled to meet desirable dissolution rates. There is a need for developing improved compositions of apixaban which exhibit desirable dissolution rates, regardless of the particle size of apixaban.

The inventors of the present invention have identified methods for resolving the issues associated with the available apixaban formulations, by developing an inventive capsule dosage form of apixaban which overcomes particle size limitations and further provides manufacturing ease, without compromising on the solubility and stability of the final formulation.

Additionally, it is desirable to develop stable pharmaceutical compositions of apixaban suitable for oral administration to human subjects, which exhibit prolonged room temperature stability without any significant loss of potency. The present invention fulfils such needs by developing stable oral compositions of apixaban to achieve an improved standard of patient care.

SUMMARY OF THE INVENTION

The present invention relates to stable pharmaceutical compositions of apixaban suitable for oral administration comprising apixaban solubilized in pharmaceutically acceptable carrier systems.

The present invention relates to stable pharmaceutical compositions of apixaban suitable for oral administration comprising apixaban in soluble form.

Another aspect of the present invention relates to stable pharmaceutical compositions of apixaban suitable for oral administration comprising apixaban dispersed in pharmaceutically acceptable carrier systems.

The present invention relates to stable pharmaceutical compositions of apixaban suitable for oral administration comprising apixaban in dispersed form.

An aspect of the present invention relates to stable pharmaceutical compositions of apixaban suitable for oral administration comprising apixaban solubilized in a pharmaceutically acceptable carrier system, wherein the pharmaceutically acceptable carrier system comprises (i) at least one solubilizing agent; and (ii) at least one pharmaceutically acceptable excipient selected from the group comprising crystallization inhibitors, stabilizers, solvents or combinations thereof.

An aspect of the present invention relates to stable pharmaceutical compositions of apixaban suitable for oral administration comprising apixaban dispersed in a pharmaceutically acceptable carrier system, wherein the pharmaceutically acceptable carrier system comprises (i) at least one solubilizing agent; and (ii) at least one pharmaceutically acceptable excipient selected from the group comprising of crystallization inhibitors, stabilizers, solvents or combinations thereof.

An aspect of the present invention relates to stable pharmaceutical compositions of apixaban suitable for oral administration comprising apixaban solubilized in a pharmaceutically acceptable carrier system, wherein the pharmaceutically acceptable carrier system comprises (i) at least one solubilizing agent; and (ii) optionally at least one pharmaceutically acceptable excipient selected from the group consisting crystallization inhibitors, stabilizers, solvents or combinations thereof.

In an aspect of the invention, apixaban is present in a therapeutically effective amount ranging from about 0.5 mg/unit dosage form to about 50 mg/unit dosage form.

In an aspect of the invention, a pharmaceutical composition is provided comprising a fill material encapsulated in a capsule shell, wherein the fill material comprises: apixaban and a pharmaceutically acceptable carrier system, wherein fill material is in the form of a liquid, wherein apixaban is uniformly dissolved or solubilized in the pharmaceutically acceptable carrier system and wherein the fill material comprises from about 0.5 mg to about 50 mg of apixaban.

Another aspect of present invention is to provide a pharmaceutical composition comprising apixaban or its pharmaceutically acceptable salt with a substantially non-aqueous carrier system and optionally pharmaceutically acceptable excipients.

In one aspect, a process for preparing stable compositions of apixaban suitable for oral administration is provided, wherein the inventive process comprises solubilizing apixaban in a solubilizing agent along with other pharmaceutically acceptable excipients to obtain a stable clear solution.

In one aspect, the pharmaceutical composition comprises fill material encapsulated in a capsule shell, wherein the capsule shell comprises a shell forming polymer, at least one plasticizer, and optionally an opacifying agent, a coloring agent, or a coating agent.

In an aspect, a pharmaceutical composition is provided comprising a fill material encapsulated in a capsule shell, wherein the fill material comprises (a) apixaban and (b) a solubilizing agent selected from the group consisting of surfactants, oils, wetting agents, polyethylene glycols, polyhydric alcohols, cyclodextrins or mixtures thereof; and wherein the capsule shell comprises (a) a shell forming polymer, (b) a plasticizer, and (c) a solvent.

In another aspect, a process for preparing a stable composition of apixaban suitable for oral administration is provided, wherein the inventive process comprises solubilizing apixaban in a solubilizing agent along with other pharmaceutically acceptable excipients to obtain a stable clear solution, and further encapsulating the obtained clear solution in a hard or soft capsule. The capsule encapsulating the apixaban solution may further be coated with a film forming polymer selected from the group consisting of hydroxypropyl methylcellulose, polyvinyl alcohol, polyvinyl pyrrolidone, hydroxyethyl cellulose, hydroxypropyl cellulose, carboxy methyl cellulose and combinations thereof. The capsule encapsulating the apixaban solution may further be coated with a functional coating using a release-rate controlling polymer selected from the group consisting of cellulose acetate phthalate, hydroxypropyl methyl cellulose acetate succinate (HPMCAS), polyvinyl alcohol, an acrylic polymer such as methacrylic acid/methacrylic acid ester copolymers such as methacrylic acid/methylmethacrylate copolymers, polyvinyl alcohol, polyacrylamides, phthalate derivatives such as acid phthalates of carbohydrates, amylose acetate phthalate, cellulose acetate phthalate, other cellulose ester phthalates, cellulose ether phthalates, hydroxypropyl cellulose phthalate, hydroxypropyl ethylcellulose phthalate, hydroxypropyl methylcellulose phthalate, methylcellulose phthalate, polyvinyl acetate phthalate, poly acrylic methacrylic acid copolymers, shellac, and vinyl acetate and crotonic acid copolymers or combinations thereof, in order to provide the desired release profile.

An aspect of the present invention relates to stable soft-gelatin capsules of apixaban, suitable for oral administration, wherein the dissolution profile of the soft-gelatin capsules is comparable with the dissolution profile of the commercially available immediate-release tablet form (Eliquis® having National Drug Code Number 0003-0893-21, 0003-0893-31, 0003-0894-21, 0003-0894-31, 0003-0894-70, 0003-0894-74, and NDA Number 202155).

An aspect of the present invention relates to a pharmaceutical composition comprising: (a) apixaban; and (b) a pharmaceutically acceptable carrier system; wherein the composition provides an in-vitro release of not less than about 70 wt % of the apixaban, within 30 minutes of dissolution in 900 mL of 0.05 M sodium phosphate buffer with 0.05% SLS (sodium lauryl sulfate) (pH 6.8) dissolution medium, measured using USP Apparatus II, at 75 RPM and at 37° C.

One aspect of the present invention relates to stable soft-gelatin capsules of apixaban, suitable for oral administration, having extended stability. In an aspect, the present invention relates to stable soft-gelatin capsules of apixaban, suitable for oral administration, wherein said compositions are stable for at least 1 month, for at least 2 months, for at least 3 months, for at least 6 months upon storage at 40° C./75% RH or at 40° C./25% RH and for at least 1 month, for at least 3 months, for at least 6 months, for at least 9 months, for at least 12 months, for at least 18 months, for at least 24 months upon storage at 25° C./60% RH.

Another aspect relates to methods to reduce the risk of stroke and systemic embolism in patients with nonvalvular atrial fibrillation; and/or for prophylaxis of deep vein thrombosis (DVT), which may lead to pulmonary embolism (PE), in patients who have undergone hip or knee replacement surgery; and/or for treatment of DVT and PE and methods to reduce the risk of recurrence of DVT and PE, by orally administering the inventive soft-gelatin capsule dosage form, comprising apixaban in a soluble form.

By way of non-limiting examples, exemplary combinations applicable to the embodiments described in this application may include any combination with one or more of the elements described above.

BRIEF DESCRIPTION OF THE DRAWINGS

FIG. 1: Brief manufacturing flow chart.

DETAILED DESCRIPTION OF THE INVENTION

Unless defined otherwise, all the technical and scientific terms used herein have the same meanings as commonly known by a person skilled in the art. In case of conflict, the definitions provided herein will prevail. Unless specified otherwise, all the percentages, portions and ratios in the present invention are on weight basis.

As used herein, the term "about" means having a value falling within an accepted standard of error of the mean when considered by one of ordinary skill in the art. Frequently, the term "about" refers to ±20%, preferably ±10%, and more preferably ±5% of the value or range to which it refers.

The term "pharmaceutically acceptable salt" refers to apixaban salts which are formed with inorganic or organic acids.

The term "pharmaceutically acceptable" substances mean those, which, according to a common medical judgment, are suitable to be in contact with a tissue of a patient without any inappropriate toxicity, irritation, allergic response, etc., have a reasonable balance between advantages and disadvantages, and can be applied to its target use effectively.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The terms "pharmaceutical composition", "pharmaceutical product", "pharmaceutical dosage form", "dosage form", "unit dosage form", "composition", "formulation", etc., refer to a composition administered to a patient in need of treatment, including but not limited to tablet, hard-gelatin capsule, soft-gelatin capsule, oral suspension, oral solution, coated hard-gelatin capsule, coated soft-gelatin capsule, enteric coated hard-gelatin capsule, enteric coated soft-gelatin capsule, coated cores, pellets, micro pellets, pills, mini-tablets, granules, spheres and the like. The capsule shells may be made up of soft-gelatin or hard-gelatin or HPMC (hydroxypropyl methylcellulose) or plant-based materials (e.g., Vegicaps®, carrageenan).

A "carrier system" herein comprises a component in which apixaban is homogeneously distributed therein. In a preferred embodiment, the drug-carrier system is encapsulated within a capsule shell that is suitable for oral administration. The carrier is "aqueous" or "non-aqueous" or "substantially non-aqueous" i.e., having no water, or in an amount of 0% to less than about 5% by weight.

As used herein, "capsule" refers to the entire inventive pharmaceutical dosage form including the capsule shell and the fill encapsulated therein. As used herein, "capsule shell" or "capsular wall" refers to both hard and soft capsule shells, made by known processes or purchased from commercial suppliers. As used herein, the term "soft-gel" or "soft-gel capsule" or "soft capsule" includes, without limitation, gelatin-free soft capsules and conventional gelatin-based soft capsules.

The shells of the soft gelatin capsules for use in the compositions described herein can be made up of a combination of gelatin, water, an opacifier and a plasticizer such as glycerin or sorbitol. The soft gelatin capsule of the present invention will be filled with an effective amount of apixaban and a pharmaceutically acceptable carrier system.

As used herein, "fill material" or "fill" refers to the composition that is encapsulated by the capsule shell that contains at least one active ingredient. The amount of fill composition typically ranges from about 150 mg to about 1250 mg, more preferably from about 200 mg to about 900 mg. Typically the fill composition fills the entire inner volume of the capsule shell.

The capsule shell can be made according to known manufacturing processes or purchased from commercially available sources. As noted above, the capsule shell of the invention includes, without limitation, gelatin-free soft capsule shells, conventional gelatin-based soft capsule shells, and carrageenan-based capsule shells, as well as hard capsule shells. There is no limitation on the materials suitable for use in the capsule shells of the invention. Preferably the capsule shell is a soft capsule shell, more preferably a gelatin-based soft capsule shell or soft-gel, made according to known manufacturing processes. The size of the capsule shell typically ranges from about 3 minim to about 22 minim, preferably from about 8 minim to about 20 minim, and more preferably from about 10 minim to about 18 minim.

As used herein, the term "apixaban" refers to apixaban free base or its pharmaceutically acceptable salts, solvates or hydrates thereof. In principle, any crystalline or amorphous form of apixaban may be used for manufacturing pharmaceutical compositions of the present invention. The apixaban drug particles used for manufacturing pharmaceutical composition of the present invention have a $D_{90}$ particle size of not less than about 90 μm, preferably not less than about 100 μm, more preferably not less than about 120 μm.

According to an embodiment of this invention, the particle size $D_{90}$ of the apixaban is more than about 89 μm. For example, according to an embodiment of this invention, the particle size $D_{90}$ of the apixaban is not less than about 100 μm, preferably not less than about 110 μm, more preferably not less than about 120 μm.

The terms "dosage", "dose unit" or "dose" as used herein means the amount of pharmaceutical formulation comprising therapeutically active agent(s) administered at a time.

By "effective amount" or "therapeutically effective amount" is meant the amount of a drug sufficient to treat, prevent, or ameliorate a condition in a subject or patient. The effective amount of apixaban or pharmaceutically acceptable salt thereof, may be determined and adjusted by a person of ordinary skill to provide the appropriate amount and dosage regimen, e.g., depending upon manner of administration, the age, body weight, sex, and/or general health of the patient.

Within the context of this invention, the term "solution" refers to a mixture of one or more substances dissolved in a dissolving liquid medium or vehicle. The solution is preferably homogeneous, in the sense that Active Pharmaceutical Ingredient (API) is essentially uniformly dissolved and distributed in the solution.

The term "solubility" means solubility of apixaban or its pharmaceutically acceptable salts in media such as water, alcohols, oils, surfactants, solubilizers, polyols, buffer, gastrointestinal simulated fluid, gastrointestinal fluid and the like.

As used herein, the term "solubilized" refers to apixaban being uniformly dissolved in a liquid medium in order to form a homogeneous system that is physically and chemically uniform throughout.

As used herein, the term "dispersed" refers to apixaban being uniformly distributed or suspended in a liquid or semi-solid medium.

The term "liquid and/or semi-solid" mentioned throughout the specification refer to apixaban and optionally, one or more pharmaceutically acceptable excipients, in the form of a solution and/or partially in the form of finely divided particles suspended freely in a suitable carrier system and encapsulated in a soft or hard-gelatin capsule.

The term "subject" refers to an animal, including a human or non-human. The terms patient and subject may be used interchangeably herein.

The terms "stable" and "stability" mean that the evolution of the product with time and/or under specific environmental conditions (i.e., temperature, humidity, etc.) has no significant effects on its quality, safety and/or efficacy for a given time period. It can be measured through formation of degradation products (impurities), variation of pH, appearance (precipitation), microbial growth, and/or color. The term "stable" may indicate physical stability and/or chemical stability.

The term "physically stable" means a solution of apixaban in pharmaceutically acceptable carrier system with no visible apixaban crystals and with no tendency to precipitate upon storage under specified conditions, e.g., at 2-8° C., room temperature, 25° C./60% RH, 40° C./75% RH, 40° C./25% RH for a specified time period of at least 1 week, 2 weeks, 1 month, 2 months, 6 months, 1 year, or 2 years.

The term "chemically stable" means no more than about 10% loss of apixaban under typical commercial storage conditions. Preferably, formulations of the present invention will have no more than about 8% loss of apixaban, more preferably, no more than about a 5% loss of apixaban, more preferably, no more than about a 3% loss of apixaban under specified conditions, e.g., at 2-8° C., or at room temperature, or at 25° C./60% RH, or at 40° C./75% RH, or at 40° C./25% RH for at least 2 months, for at least 3 months, at least 6 months, at least 9 months, at least 12 months, at least 15 months, at least 18 months, at least 21 months, at least 24 months, at least 30 months and at least 36 months.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

The term "bioavailability" indicates the extent to which a drug or another substance is utilized by a target tissue after administration. For example, "bioavailability" may refer to the fraction of drug absorbed following administration to a subject or patient under fed or fasted state.

Apixaban is a poorly water-soluble compound with non-ionizable functional groups. It has a low aqueous solubility of 40-50 μg/mL in water with a pH independent solubility profile. Its solubility is very low throughout the physiological pH range of about 1.0 to about 8.0.

It is difficult to formulate drugs of low water solubility such as apixaban. Conventional formulation strategies are no longer adequate or useful to achieve the acceptable solubility and in turn bioavailability. However, a number of alternative technologies are being developed that often allow for a faster onset of action as the active ingredient is already in a liquid form (solubilized or dispersed), which tends to speed up absorption.

Carrier systems play a major role in the formulation of low water-soluble drugs, such as apixaban, as it affects the physical stability of the formulation, dissolution, and release of active from the formulation at a desired rate. The ingredients of the carrier system play an important role in formulation since apixaban is a drug having low solubility.

After rigorous experimentation, the inventors of the present invention have found that the solubility and stability of apixaban can be improved by developing a liquid and/or semi-solid composition, preferably a liquid form of apixaban with a suitable carrier system, comprising one or more solubilizing agents. Extensive solubility studies were conducted to identify a solubilizing agent that solubilizes unit dose of apixaban in a pharmaceutical composition. Moreover, this solubilizing agent should also maintain apixaban in a dissolved state at varying temperatures to which the formulation may be exposed while shipping and handling by the patients.

Apixaban saturation solubility study data, as tabulated below, illustrates the best possible solubilizing agents that are utilized in the present invention.

TABLE 1

Saturation solubility of apixaban

| S. No. | Solubility enhancing agents | *mg/g |
| --- | --- | --- |
| 1 | Glycerine | 0.33 |
| 2 | Propylene glycol | 1.45 |
| 3 | PEG-400 | 2.92 |
| 4 | Polysorbate-80 | 0.98 |
| 5 | Glycerine + Propylene glycol (60:40) | 0.85 |
| 6 | Glycerine + PEG-400 (80:20) | 0.3 |
| 7 | Glycerine + Polysorbate-80 (80:20) | 0.41 |

TABLE 1-continued

Saturation solubility of apixaban

| S. No. | Solubility enhancing agents | *mg/g |
|---|---|---|
| 8 | PEG-400 + Polysorbate-80 (40:60) | 1.94 |
| 9 | Labrasol ® ALF | 1.55 |
| 10 | Kolliphor ® EL | 0.56 |
| 11 | Sodium lauryl sulphate (6.66% solution in Purified water) | 4.18 |
| 12 | Povidone K 30 (6.66% solution in Purified water) | 0.17 |

*Quantity of apixaban dissolved per gram of solubility enhancing agent

The present application relates to stable oral pharmaceutical compositions of apixaban, wherein apixaban is present in an amount of about 0.5 mg per unit dosage form or more. In an embodiment, pharmaceutical composition of the present invention comprises apixaban, wherein apixaban is present in an amount ranging from about 0.5 mg/unit dosage form to about 50.0 mg/unit dosage form.

In a preferred embodiment, apixaban in the inventive composition is present in an amount of about 0.5 mg/unit dosage form, about 1.0 mg/unit dosage form, about 2.0 mg/unit dosage form, about 2.5 mg/unit dosage form, about 3.0 mg/unit dosage form, about 4.0 mg/unit dosage form, about 5.0 mg/unit dosage form, about 7.5 mg/unit dosage form, about 10.0 mg/unit dosage form, about 15.0 mg/unit dosage form, about 20.0 mg/unit dosage form, about 25.0 mg/unit dosage form, about 30 mg/unit dosage form, about 35 mg/unit dosage form, about 40 mg/unit dosage form, about 45 mg/unit dosage form, or about 50 mg/unit dosage form.

Preferably, the pharmaceutical composition of the present invention will be provided in a dosage form that is suitable for oral administration, including but not limited to a tablet, hard-gelatin capsule, soft-gelatin capsule, oral suspension, oral solution, coated hard-gelatin capsule, coated soft-gelatin capsule, enteric coated hard-gelatin capsule, enteric coated soft-gelatin capsule, coated cores, pellets, micro pellets, pills, mini-tablets, granules, spheres, and the like. The pharmaceutical compositions may be formulated according to conventional pharmaceutical practice.

In one preferred embodiment, the pharmaceutical composition according to the present invention is in the form of capsules, including but not limited to, soft-gelatin, hard-gelatin, HPMC, polysaccharide or starch; as plugged, welded, banded, or glued capsules; of different size, colour, and water content.

Another embodiment provides methods to reduce the risk of stroke and systemic embolism in patients with nonvalvular atrial fibrillation; and/or for prophylaxis of deep vein thrombosis (DVT), which may lead to pulmonary embolism (PE), in patients who have undergone hip or knee replacement surgery; and/or for treatment of DVT and PE and methods to reduce the risk of recurrence of DVT and PE, by orally administering the soft-gelatin capsule, comprising apixaban in a soluble form.

In an embodiment, the present invention provides a stable pharmaceutical composition suitable for oral administration, comprising apixaban solubilized in a pharmaceutically acceptable carrier system.

In another embodiment, the present invention provides a stable pharmaceutical composition suitable for oral administration, comprising apixaban dispersed in a pharmaceutically acceptable carrier system.

In another embodiment, the present invention provides a pharmaceutical composition comprising apixaban or its pharmaceutically acceptable salt with a substantially non-aqueous carrier system and optionally pharmaceutically acceptable excipients.

In an embodiment, a pharmaceutical composition is provided comprising a fill material encapsulated in a capsule shell, wherein the fill material comprises: apixaban and a pharmaceutically acceptable carrier system, wherein fill material is in the form of a liquid, wherein apixaban is uniformly dissolved or solubilized in the pharmaceutically acceptable carrier system and wherein the fill material comprises from about 0.5 mg to about 50 mg of apixaban.

In an embodiment, the present invention relates to stable pharmaceutical compositions of apixaban suitable for oral administration comprising apixaban solubilized in a pharmaceutically acceptable carrier system, wherein the pharmaceutically acceptable carrier system comprises (i) at least one solubilizing agent; and (ii) optionally at least one pharmaceutically acceptable excipient selected from the group comprising crystallization inhibitors, stabilizers, solvents or combinations thereof.

In another embodiment, the present invention relates to stable pharmaceutical compositions of apixaban suitable for oral administration comprising apixaban solubilized in a pharmaceutically acceptable carrier system, wherein the pharmaceutically acceptable carrier system comprises (i) at least one solubilizing agent; and (ii) at least one pharmaceutically acceptable excipient selected from the group comprising crystallization inhibitors, stabilizers, solvents or combinations thereof.

In yet another embodiment, the present invention relates to stable pharmaceutical compositions of apixaban suitable for oral administration comprising apixaban dispersed in a pharmaceutically acceptable carrier system, wherein the pharmaceutically acceptable carrier system comprises (i) at least one solubilizing agent; and (ii) optionally at least one pharmaceutically acceptable excipient selected from the group consisting of crystallization inhibitors, stabilizers, solvents or combinations thereof.

In an embodiment, the present invention relates to stable pharmaceutical compositions suitable for oral administration comprising apixaban solubilized in a pharmaceutically acceptable carrier system, wherein the composition is in a semi-solid or a liquid form.

In yet another embodiment, the present invention relates to stable pharmaceutical compositions suitable for oral administration comprising apixaban dispersed in a pharmaceutically acceptable carrier system, wherein the composition is in a semi-solid or a liquid form.

In an embodiment, the present invention relates to stable hard capsules of apixaban, suitable for oral administration, comprising apixaban solubilized in a pharmaceutically acceptable carrier system, wherein the pharmaceutically acceptable carrier system comprises (i) at least one solubilizing agent; and (ii) optionally at least one pharmaceutically acceptable excipient selected from the group comprising crystallization inhibitors, stabilizers, solvents or combinations thereof.

In another embodiment, the present invention relates to stable soft capsules of apixaban, suitable for oral administration, comprising apixaban solubilized in a pharmaceutically acceptable carrier system, wherein the pharmaceutically acceptable carrier system comprises (i) at least one solubilizing agent; and (ii) optionally at least one pharmaceutically acceptable excipient selected from the group comprising crystallization inhibitors, stabilizers, solvents or combinations thereof.

Suitable solubilizing agents used in the present invention include one or more surfactants, oils, wetting agents, polyethylene glycols, polyhydric alcohols, cyclodextrins or mixtures thereof. In a preferred embodiment, concentration of the solubilizing agent ranges from about 0.1% to about 90%, based on total weight of the pharmaceutical composition.

Suitable surfactants used in the present invention may be ionic or non-ionic surface-active agents. Suitable ionic surfactants include, but are not limited to, those containing carboxylate, sulfonate and sulfate ions. Examples of anionic surfactants include, but are not limited, sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; alkyl sulfates such as sodium lauryl sulfate; quaternary ammonium compounds such as benzalkonium chloride, benzethonium chloride, cetrimonium bromide, stearyl dimethylbenzyl ammonium chloride. In a preferred embodiment, the concentration of ionic surfactant ranges from about 0.1% to about 95%, based on total weight of the pharmaceutical composition.

Suitable nonionic surfactants include, but are not limited to, ethylene glycol monostearate, propylene glycol myristate, glyceryl monostearate, glyceryl stearate, polyglyceryl-4-oleate, sorbitan acylate, sucrose acylate, polyethylene glycol dilaurate, polyethylene glycol monolaurate, polysorbates, polyoxyethylene octylphenylether, polyethylene glycol cetyl ether, polyoxyethylene tridecyl ether, polypropylene glycol butyl ether, stearoyl monoisopropanolamide, polyoxyethylene hydrogenated tallow amide, polyoxyl-ethylated castor oils (Cremophor®), polyoxyethylene esters of 12-hydroxystearic acid (Solutol®) and PEGylated glycerides (Labrasol®), block copolymers of poly(ethylene oxide) (PEO) and poly(propylene oxide) (Poloxamers). In a preferred embodiment, the concentration of non-ionic surfactant ranges from about 0.1% to about 95%, based on total weight of the pharmaceutical composition.

In some embodiments, one or more phospholipid surfactant may be used as a surfactant. Exemplary phospholipids used in the present inventive compositions are lecithin, phosphatidylcholine (PC), lysophosphatidylcholine (LPC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof. In another embodiment, the phospholipid surfactant may be Phosal® which comprises, phosphatidylcholine, lysophosphatidylcholine, mono- and diglycerides from sunflower oil, soy fatty acids, ethanol, and ascorbyl palmitate. In a preferred embodiment, the concentration of phospholipid surfactant ranges from about 0.1% to about 95%, based on total weight of the pharmaceutical composition.

In some embodiments, one or more "oil" may be used as a solubilizing agent. The term "oil" as used herein means an agent that functions as a non-aqueous solvent or solubility enhancing agent, particularly depending on the amount of oil used in inventive compositions as described herein. More specifically, oils may include, for example and without limitation, medium-chain fatty acids, medium-chain fatty acid esters of glycerol (e.g. mono, di or triglyceride), medium-chain fatty acid esters of polyethylene glycol, medium-chain fatty acid esters of propylene glycol, long chain fatty acids, long-chain fatty acid esters of glycerol (e.g. mono, di or triglyceride), long-chain fatty acid esters of polyethylene glycol, long-chain fatty acid esters of propylene glycol or combinations thereof. The term "medium-chain" is used to describe the aliphatic chain length of fatty acid containing molecules. The term "medium-chain" as used herein means any medium-chain carbon-containing (i.e., $C_4$-$C_{12}$ containing) substance, including $C_4$-$C_{12}$ fatty acid esters of glycerol, fatty acids, and mono-, di-, and tri-glycerides of such substances. The term "long-chain" is used to describe the aliphatic chain length of fatty acid containing molecules. The term "long-chain" as used herein means any long chain carbon-containing (i.e., $C_{14}$-$C_{24}$ containing) substance, including $C_{14}$-$C_{24}$ fatty acid esters of glycerol, fatty acids, and mono-, di-, and tri-glycerides of such substances. In a preferred embodiment, the concentration of "oil" ranges from about 0.1% to about 95%, based on total weight of the pharmaceutical composition.

Pharmaceutically acceptable medium chain oils include, without limitation, polyethylene glycol glyceride (Labrasol® ALF and Gelucire®); a caprylic/capric triglyceride; (Miglyol® including Miglyol® 810, 812, 816 and 829); a caproic/caprylic/capric/lauric triglyceride; a caprylic/capric/linoleic triglyceride; a caprylic/capric/succinic triglyceride; propylene glycol monocaprylate; propylene glycol monocaprate (Capmul®; Capmul®); propylene glycol dicaprylate; propylene glycol dicaprylate; medium chain mono- and di-glycerides (Capmul®); a diethylene glycol mono ester (Transcutol®); diethylene glycol monoethyl ether; esters of saturated coconut and palm kernel oil and derivatives thereof; triglycerides of fractionated vegetable fatty acids, and combinations and derivatives thereof. In a preferred embodiment, the concentration of "medium chain oil" ranges from about 0.1% to about 95%, based on total weight of the pharmaceutical composition.

Pharmaceutically acceptable long chain oils include, without limitation, glyceryl mono-myristate (Nikkol®), glyceryl mono-palmitate (Emalex®), glyceryl monooleate (Rylo® series, Dimodan® series, Emuldan®, ALDO®, Kessco®, Monomuls®, Tegino®, Drewmulse® GMO, Atlas®, GMOrphic®, ADM DMG-40, 70, and 100, Peceol®, Hodag®, Myverol®), glyceryl mono-, dioleate (Capmul®), glyceryl dioleate (Capmul®), glyceryl mono-linoleate (Maisine®; Myverol®), glycerol mono-stearate (Capmul®, Myvaplex®, Imwitor®, Cutina®, Aldo®, Nikkol®), glyceryl palmitic/stearic (Cutina®, Estagel®), glyceryl mono-α-linolenic acid, glyceryl mono-elaidate, glyceryl mono-vaccenate, glyceryl mono-linoelaidate, glyceryl mono-arachidonate, glyceryl mono-eicosapentaenoate, glyceryl mono-erucic acid, glyceryl mono-docosahexaenoic acid or mixtures thereof. In a preferred embodiment, the concentration of "long chain oil" ranges from about 0.1% to about 95%, based on total weight of the pharmaceutical composition.

Wetting agents can also act as solubilizing agents. Examples of wetting agents include, but are not limited to, triacetin, vitamin E TPGS, ammonium salts, oleic acid, glyceryl monostearate, sorbitan monooleate, sorbitan monolaurate, triethanolamine oleate, polyoxyethylene sorbitan monooleate, polyoxyethylene sorbitan monolaurate, docusate sodium, sodium oleate or mixtures thereof. In a preferred embodiment, the concentration of wetting agent ranges from about 0.1% to about 95%, based on total weight of the pharmaceutical composition.

In an embodiment, liquid or semisolid, low/intermediate viscous polyethylene glycols are used as solubilizing agents. A polyethylene glycol as referred herein is a polymer of ethylene glycol formed by the reaction of ethylene oxide and water. Non-limiting examples of polyethylene glycols that can be used in the present apixaban inventive compositions are polyethylene glycol 200, polyethylene glycol 300, polyethylene glycol 400, polyethylene glycol 600, polyethylene glycol 1000, polyethylene glycol 1450, polyethylene glycol 3300, polyethylene glycol 6000, polyethylene glycol 8000, polyethylene glycol 10000 or mixtures thereof. In a preferred embodiment, the amount of polyethylene glycol ranges from about 0.1% to about 95%, based on total weight of the pharmaceutical composition.

A mono or polyhydric alcohol as referred to herein is a compound with one or more than one hydroxyl group. Non-limiting examples of mono or polyhydric alcohols that can be used as solubilizing agents are glycerin, methanol, ethanol, n-octanol, i-octanol, octadecanol, 1,6-hexanediol, ethylene glycol, propylene glycol, neopentyl glycol, thiodiethylene glycol, diethylene glycol, triethylene glycol or mixtures thereof. In a preferred embodiment, the concentration of mono or polyhydric alcohol ranges from about 0.1% to about 95%, based on total weight of the pharmaceutical composition.

The cyclodextrins can be selected from the group consisting of α-cyclodextrin, β-cyclodextrin, δ-cyclodextrin, ε-cyclodextrin or their derivatives. In a preferred embodiment, the concentration of cyclodextrins ranges from about 0.1% to about 95%, based on total weight of the pharmaceutical composition.

The present invention involves the use of a solubilizing agent for solubilization of the active ingredient (i.e. apixaban). However, apixaban may crystallize over time resulting in loss of desired properties and shortened shelf life. The present invention uses "crystallization inhibitors" in order to promote the physical stability of apixaban in the final encapsulated solution. The term "crystallization inhibitors" as used herein, inhibits the crystallization of the active ingredient thereby making the formulation physically stable for a longer period of time. As crystallization inhibitors, highly dispersed silicon dioxide or macromolecular substances are suitable. Illustrative macromolecular substances include, but are not limited to, for example, polyvinylpyrrolidone (PVP), polyvinyl alcohol, hydroxypropyl cellulose, hydroxypropyl methylcellulose, ethyl cellulose, sodium carboxymethylcellulose, gelatin, starch (derivatives), copolymers of vinyl acetate and of vinylpyrrolidone, polyethylene glycols, benzyl alcohol, mannitol, glycerine, sorbitol, lecithin or polyoxyethylenated esters of sorbitan; or dextrins and dextrans (such as, for example, α-, β- and γ-cyclodextrin, dimethyl-β-cyclodextrin and 2-hydroxypropyl-β-cyclodextrin), sterols (such as cholesterol) or bile acids (such as cholic acid or lithocholic acid) can be used. The preferred crystallization inhibitors in the present invention are polyvinylpyrrolidones and glycerine. In a preferred embodiment, the concentration of crystallization inhibitors ranges from about 0.1% to about 95%, based on total weight of the pharmaceutical composition.

The pharmaceutical compositions of the present invention may additionally contain an anti-oxidant which inhibits oxidation and thus is used to prevent the deterioration of preparations by the oxidative process. Such compounds include by way of example and without limitation, sodium bisulfate, ascorbic acid, ascorbyl palmitate, glycine, L-cysteine hydrochloride, L-methionine, butylated hydroxy anisole, butylated hydroxytoluene, hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite, alpha-tocopherol, and others known to those of ordinary skill in the art. The concentration of anti-oxidant ranges from about 0.1% to about 30% based on total weight of the pharmaceutical composition.

The pharmaceutical compositions of the present invention can optionally include one or more solvents, i.e., additives, to increase the solubility of the active ingredient or other composition components in the carrier. Suitable solvents for use in the compositions of the present invention include without limitation, acids (e.g., acetic acid, oleic acid, propionic acid, butyric acid, lactic acid, pyruvic acid, oxalic acid, malic acid, malonic acid, succinic acid, maleic acid, fumaric acid, tartaric acid, citric acid, benzoic acid, cinnamic acid, mandelic acid, salicylic acid, etc.), alcohols and polyols, (e.g., ethanol, isopropanol, butanol, benzyl alcohol, ethylene glycol, propylene glycol, butanediols and isomers thereof, glycerol, pentaerythritol, sorbitol, mannitol, dimethyl isosorbide, polyethylene glycol, polypropylene glycol, polyvinyl alcohol, cellulose derivatives, etc.). The amount of solvent that can be included in compositions ranges from about 0.1% to about 80%, based on total weight of the pharmaceutical composition.

The pharmaceutical composition of the present invention may contain a "stabilizing agent" or "stabilizer". The terms "stabilizing agent" or "stabilizer" as used herein inhibits, prevents, slows down, or reduces the degradation of apixaban. More specifically, stabilizing agents include amino acids such as glycine, alanine, glutamate, sodium glutamate, L-arginine, lysine, L-cysteine or methionine; sodium chloride or sodium sulfate salts; ethylenediaminetetraacetic acid (EDTA), metal ions such as zinc, magnesium and calcium or mixtures thereof; natural or synthetic gums, cellulosic derivatives such as carboxy methyl cellulose, ethyl cellulose, hydroxyethyl cellulose, hydroxyl propyl cellulose, hydroxyl propyl methylcellulose, methyl cellulose, polyanionic cellulose; cyclodextrins; sugars; sugar alcohols; monosaccharides, disaccharides or polysaccharides or combinations thereof. The concentration of stabilizer ranges from about 5% to about 70%, based on total weight of the pharmaceutical composition. In an embodiment described herein, the pharmaceutical composition comprises a fill material encapsulated in a capsule shell, wherein the capsule shell comprises a shell-forming polymer, a plasticizer, a solvent, optionally, an opacifying agent, a coloring agent, a coating agent, a release rate controlling agent or a pharmaceutical excipient. The term "shell-forming polymer" as used herein refers to polymeric materials that can be cross-linked, dried and formed into shells that are, for example, part of a capsule. In another embodiment described herein, the soft capsule shell comprises: (a) about 25% to about 60% of at least one shell-forming polymer based on the total weight of the capsule shell; (b) about 5% to about 40% of at least one plasticizer based on the total weight of the capsule shell; (c) about 5% to about 40% of a solvent based on the total weight of the capsule shell; (d) optionally, an opacifying agent, a coloring agent, a release rate controlling agent or combination thereof.

Shell-forming polymers that are useful for creating capsule shells are gelatin, hydroxypropyl methylcellulose (HPMC) or carrageenan (e.g., iota carrageenan and kappa carrageenan) or chitosan. The capsule shell composition of the invention can contain at least one plasticizer selected from the from the group comprising sorbitol, glycerol, polyethylene glycol, poly-alcohols with 3 to 6 carbon atoms, citric acid, citric acid esters such as triethyl citrate, and combinations thereof. The capsule shell composition is made by dissolving or dispersing shell-forming polymer, a plasticizer, optionally, an opacifying agent, a coloring agent, a coating agent, a release rate controlling agent or a pharmaceutical excipient in a solvent such as water and/or an alcohol. In another embodiment described herein, the capsule shell comprises gelatin, glycerol, sorbitol solution, water, and optionally, titanium oxide, and a coloring agent.

The invention also relates to a process of manufacturing a shell composition into soft capsules. The process includes preparing a solution comprising a shell-forming polymer and mixing with appropriate plasticizers to form a gel mass; casting gel mass into films or ribbons using heat-controlled drums or surfaces; and manufacturing a soft capsule using rotary die technology.

For the purposes of the present invention, the presence of specific plasticizers, i.e. sorbitol and glycerine in a specific weight ratio with each other and, as a whole, with respect to the total weight of the capsule shell (in the dry state) is important. Specifically, in the soft capsule according to any of the herein disclosed embodiments of the present invention, the weight ratio of glycerine:sorbitol ranges from about 0.2:1 to 3:1 or from about 1:0.2 to about 1:3. In an embodiment the weight ratio of glycerine:sorbitol is about 0.2:1, about 0.5:1, about 1:1, about 1.5:1, about 2:1, about 2.5:1, about 3:1, about 1:0.2, about 1:0.5, about 1:1.5, about 1:2, about 1:2.5, or about 1:3; moreover, the total amount by weight of glycerine and sorbitol with respect to the weight of the capsule shell (in the dry state) is within a range of about 5% to about 50%, preferably it is between about 10% and about 30%, more preferably between about 15% and about 25%.

In an embodiment, a phyarmaceutical composition is provided comprising a fill material encapsulated in a capsule shell, wherein the fill material comprises (a) apixaban and (b) a solubilizing agent selected from the group consisting of surfactants, oils, wetting agents, polyethylene glycols, polyhydric alcohols, cyclodextrins or mixtures thereof; and wherein the capsule shell comprises (a) a shell forming polymer, (b) a plasticizer, and (c) a solvent.

The pharmaceutical composition of the present invention containing the fill material and capsule shell may further contain a seal coat comprising a suitable seal forming agent which may be selected from among cellulosic polymers (such as hydroxypropyl methylcellulose, hydroxypropyl cellulose, methylcellulose, carboxymethyl cellulose, polyvinylpyrrolidone, polysaccharide polymer such as Pullulan® and polyacrylamides, etc. A seal-coat composition may comprise a seal-forming polymer, water and/or an alcohol as a vehicle, and optionally one or more adjuvants such as are known in the film-coating art. The functional coat composition is made by dissolving or dispersing seal coating agent, a plasticizer, a solvent, optionally, an opacifying agent, a coloring agent, or a pharmaceutical excipient in solvents such as water and/or an alcohol as a vehicle. The total amount of seal coating agent with respect to the weight of the pharmaceutical composition is within a range of about 5% to about 50%, preferably it is between about 10% and about 30%, more preferably between about 10% and about 25%.

The pharmaceutical composition of the present invention containing the fill material and capsule shell may further contain a functional coating comprising a suitable release-rate controlling coating agent, which may be selected from among cellulosic polymers (such as hydroxypropyl methylcellulose, hydroxypropyl cellulose, methylcellulose, ethylcellulose, hydroxyethyl cellulose, cellulose acetate phthalate, sodium ethyl cellulose sulfate, carboxymethyl cellulose, polyvinylpyrrolidone, hydroxypropyl methyl cellulose acetate succinate (HPMCAS) polymer), polyvinylpyrrolidone, polyvinyl alcohol, polysaccharide polymer such as Pullulan® and an acrylic polymers such as methacrylic acid/methacrylic acid ester copolymers such as and methacrylic acid/methylmethacrylate copolymers, (such as Eudragit® E polymers, Eudragit® RL polymers, Eudragit® RS polymers, Eudragit® NE polymers, Eudragit® L polymers, Eudragit® S polymers, Eudragit® FL polymers, Eudragit® FS polymers, Eudragit® L100-55, Eudragit® L-30, etc.), polyvinyl alcohol, polyacrylamides, phthalate derivatives (such as acid phthalates of carbohydrates, amylose acetate phthalate, cellulose acetate phthalate, other cellulose ester phthalates, cellulose ether phthalates, hydroxypropylcellulose phthalate, hydroxypropyl ethylcellulose, ethyl cellulose phthalate, hydroxypropyl methylcellulose phthalate, methylcellulose phthalate, polyvinyl acetate phthalate), poly acrylic methacrylic acid copolymers, shellac, and vinyl acetate and crotonic acid copolymers etc. The functional coat composition is made by dissolving or dispersing a release-rate controlling coating agent, a plasticizer, optionally, an opacifying agent, a coloring agent, a coating agent, a release rate controlling agent or a pharmaceutical excipient in solvents such as water and/or an alcohol as a vehicle. The total amount of release rate controlling agent with respect to the weight of the pharmaceutical composition is within a range of about 5% to about 50%, preferably it is between about 10% and about 30%, more preferably between about 10% and about 25%.

The functional coat compositions provided herein also can include a "pore former" or "pore forming agents". When present, a pore former is present at a weight of about 0.1 to about 30% by total weight of the pharmaceutical composition, particularly at a weight of at or about 0.25% to at or about 20% by weight of the total pharmaceutical composition. In some embodiments, the ratio of pore former to release rate controlling polymer in the functional coat component is from at or about 1:1 to at or about 1:12. In one embodiment, the ratio of pore former to release rate controlling polymer in the functional coat component is at or about 1:1, at or about 1:2, at or about 1:3, at or about 1:4, at or about 1:5, at or about 1:6, at or about 1:7, at or about 1:8, at or about 1:9, at or about 1:10, at or about 1:11, at or about 1:12. A pore former as disclosed herein may include at least one polymeric pore former, such as hydroxyalkyl cellulose, hydroxypropyl methylcellulose, hydroxypropyl cellulose, polyethylene glycols, polyvinyl alcohol, povidone, copovidone, lactose monohydrates, microcrystalline cellulose, alginates such as potassium or sodium alginates, and poloxamers.

In one embodiment of the present invention, the seal or functional coating composition may comprise one or more anti-tacking agents which helps in improving the flow characteristics of the compositions and thereby reduces the problem of adhering to a user's mouth or to other dosage units. Examples of suitable anti-tacking agents include, but are not limited to: stearates, such as magnesium stearate, calcium stearate, and sodium stearate; stearic acid; talc; cornstarch; colloidal silicon dioxide; Vitamin E TPGS (d-alpha tocopheryl polyethylene glycol 1000 succinate); waxes; boric acid; sodium benzoate; sodium acetate; sodium chloride; DL-Leucine; sodium oleate; sodium lauryl sulfate; magnesium lauryl sulfate; and combinations thereof. In yet another embodiment of the present invention, the seal or functional coating compositions may comprise opacifying agents which help to provide film coatings with excellent brightness, whiteness, and/or opacity. Examples of suitable opacifying agents include, but are not limited to: titanium dioxide, zinc oxides, dicalcium phosphate, dicalcium phosphate dehydrate, tricalcium phosphate, calcium carbonate, or combinations thereof. Anti-tacking agents or opacifying agents generally are present in amounts of about 0.01% to about 20% by weight of the coating film composition.

The formulations of the present invention may optionally further include a preservative, antioxidant, acidifying agent, alkalizing agent, plasticizers, buffering agent, bulking agent, complexing agent, cryoprotectant, chelating agent, density modifier, electrolyte, volatility modifier, viscosity modifier, antifoaming agent, coloring agent and other excipients known by those of ordinary skill in the art for use in pharmaceutical formulations.

In one embodiment, the present invention provides stable pharmaceutical compositions comprising apixaban solubilized in a pharmaceutically acceptable carrier system wherein pharmaceutically acceptable carrier system comprises (i) polyethylene glycol (ii) optionally one or more other solubilizing agents and (iii) optionally other pharmaceutically acceptable excipients.

In another embodiment, the present invention provides stable pharmaceutical compositions comprising apixaban dispersed in a pharmaceutically acceptable carrier system wherein pharmaceutically acceptable carrier system comprises (i) polyethylene glycol (ii) optionally one or more other solubilizing agents and (iii) optionally other pharmaceutically acceptable excipients.

In an embodiment, a pharmaceutical composition is provided comprising a fill material encapsulated in a capsule shell, wherein the fill material comprises (a) apixaban and (b) a solubilizing agent selected from the group comprising surfactants, wetting agents, crystallization inhibitors, polyethylene glycols, polyhydric alcohols, cyclodextrins, and mixtures thereof; and wherein the capsule shell is a gelatin capsule coated with a functional coating, wherein the pharmaceutical composition does not provide controlled release of apixaban.

In an embodiment, a pharmaceutical composition is provided comprising a fill material encapsulated in a capsule shell, wherein the fill material comprises (a) apixaban and (b) a solubilizing agent selected from the group comprising surfactants, crystallization inhibitors, wetting agents, polyethylene glycols, polyhydric alcohols, cyclodextrins, and mixtures thereof; and wherein the capsule shell is a gelatin capsule coated with a functional coating, wherein the pharmaceutical composition is not an osmotic formulation.

In an embodiment, a pharmaceutical composition is provided comprising a fill material encapsulated in a capsule shell, wherein the fill material comprises (a) apixaban and (b) a solubilizing agent selected from the group comprising, surfactants, crystallization inhibitors, wetting agents, polyethylene glycols, polyhydric alcohols, cyclodextrins, and mixtures thereof; and wherein the capsule shell is a gelatin capsule coated with a functional coating, wherein the pharmaceutical composition is not a matrix formulation.

In an embodiment, a pharmaceutical composition is provided comprising a fill material encapsulated in a capsule shell, wherein the fill material comprises (a) apixaban and (b) a solubilizing agent selected from the group comprising surfactants, crystallization inhibitors, wetting agents, polyethylene glycols, polyhydric alcohols, cyclodextrins, and mixtures thereof; and wherein the capsule shell is a gelatin capsule coated with a functional coating, wherein the pharmaceutical composition is not a multiparticulate formulation.

In an embodiment, a pharmaceutical composition is provided comprising a fill material encapsulated in a capsule shell, wherein the fill material comprises (a) apixaban and (b) a solubilizing agent selected from the group consisting of surfactants, oils, wetting agents, polyethylene glycols, polyhydric alcohols, cyclodextrins or mixtures thereof; and wherein the capsule shell is a gelatin capsule coated with a functional coating comprising ethyl cellulose, hydroxypropyl methylcellulose, polyethylene glycol, talc, and lactose.

In an embodiment, a pharmaceutical composition is provided comprising a fill material encapsulated in a capsule shell, wherein the fill material comprises (a) apixaban and (b) a solubilizing agent selected from the group consisting of surfactants, oils, wetting agents, crystallization inhibitors, polyethylene glycols, polyhydric alcohols, cyclodextrins or mixtures thereof; and wherein the capsule shell is a gelatin capsule coated with a functional coating comprising ammonio methacrylate copolymer type A® (Eudragit RL30D), hydroxypropyl methylcellulose, polyethylene glycol, talc, and lactose.

In an embodiment, a pharmaceutical composition is provided comprising a fill material encapsulated in a capsule shell, wherein the fill material comprises: (a) apixaban in an amount of about 5 mg, (b) polyethylene glycol-400 in an amount of about 500 mg, (c) propylene glycol USP in an amount of about 60 mg, (d) triacetin, USP in an amount of about 25 mg; wherein the capsule shell comprises gelatin in an amount of about 44% by weight of the capsule shell, 70% sorbitol solution in an amount of about 10% by weight of the capsule shell, glycerin in an amount of about 10% by weight of the capsule shell, and water in an amount of about 36% by weight of the capsule shell; and wherein the functional coating comprises ethyl cellulose in an amount of about 15.9 mg, hydroxypropyl methylcellulose in an amount of about 35.8 mg, polyethylene glycol in an amount of about 5.2 mg, talc in an amount of about 10.3 mg, and lactose in an amount of about 27.8 mg.

In an embodiment, a pharmaceutical composition is provided comprising a fill material encapsulated in a capsule shell, wherein the fill material comprises: (a) apixaban, (b) polyethylene glycol-400, (c) propylene glycol, (d) triacetin, and (e) polyvinylpyrrolidone; wherein the capsule shell comprises gelatin, sorbitol solution, glycerin, and water; and wherein the functional coating comprises ammonio methacrylate copolymer type A® (Eudragit RL30D), hydroxypropyl methylcellulose, polyethylene glycol, talc, and triethyl citrate.

In am embodiment, a pharmaceutical composition is provided comprising a fill material encapsulated in a capsule shell, wherein the fill material comprises: (a) apixaban in an amount of about 5 mg, (b) polyethylene glycol-400 in an amount of about 500 mg, (c) propylene glycol in an amount of about 60 mg, (d) triacetin in an amount of about 25 mg, (e) polyvinylpyrrolidone in an amount of about 10 mg; wherein the capsule shell comprises gelatin in an amount of about 70% by weight of the capsule shell, sorbitol solution in an amount of about 10% by weight of the capsule shell, glycerin in an amount of about 10% by weight of the capsule shell, and water in an amount of about 10% by weight of the capsule shell; and wherein the functional coating comprises ammonio methacrylate copolymer type A® (Eudragit RL30D) in an amount of about 21.8 mg, hydroxypropyl methylcellulose in an amount of about 26.0 mg, polyethylene glycol in an amount of about 6.5 mg, talc in an amount of about 2.1 mg, and triethyl citrate in an amount of about 6.5 mg.

In an embodiment, a pharmaceutical composition is provided comprising a fill material encapsulated in a capsule shell, wherein the fill material comprises: (a) apixaban in an amount of about 2.5 mg, (b) polyethylene glycol-400 in an amount of about 500 mg, (c) propylene glycol in an amount of about 60 mg, (d) triacetin in an amount of about 25 mg, (e) polyvinylpyrrolidone in an amount of about 10 mg; wherein the capsule shell comprises gelatin in an amount of about 70% by weight of the capsule shell, sorbitol solution in an amount of about 10% by weight of the capsule shell, glycerin in an amount of about 10% by weight of the capsule shell, and water in an amount of about 10% by weight of the capsule shell; and wherein the functional coating comprises ammonio methacrylate copolymer type A® (Eudragit RL30D) in an amount of about 21.8 mg, hydroxypropyl methylcellulose in an amount of about 26.0 mg, polyethylene glycol in an amount of about 6.5 mg, talc in an amount of about 2.1 mg, and triethyl citrate in an amount of about 6.5 mg.

In an embodiment, the present invention provides a process for preparation of a stable, pharmaceutical compositions of apixaban for oral administration, wherein the process comprises:

(a) mixing together one or more solubilizing agents, (b) optionally adding crystal growth inhibitors to the above mix, (c) adding apixaban to the above mix, (d) optionally adding one or more other pharmaceutically acceptable excipients, (e) stirring the mixture to obtain a clear solution, (f) encapsulating the solution in a hard or soft capsule shell and (g) the capsule encapsulating apixaban solution may further be coated with a functional coating in order to provide the desired release profile.

The stable pharmaceutical compositions of present application may be filled into any suitable pharmaceutically acceptable containers. For example, the pharmaceutically acceptable container may be selected from group comprising bottles with or without desiccant or foil-on-foil blister packaging.

The bottle can be made of any material convenient with the storage and the use requirements comprising polymers, metal and glass and so on. It is of importance that the bottle material does not interfere with the components of the formulation as disclosed herein.

The cap (or closure) is any article for closing a suitably shaped opening. It encompasses, but is not limited to, childproof closures, waterproof closures, solid caps, plastic or polymeric caps. In an embodiment, the cap is screwed on the bottle top or interlocked with the top of the bottle. A sealing element may be required for the tightness of the system bottle-cap. This element can be supplied on its own and further fit in the bottle-neck, or around the cap, or it can be previously adapted to the bottle or the cap.

In an embodiment, the pharmaceutically acceptable container may be a bottle, wherein the bottle is selected from group consisting of a glass bottle and a plastic bottle. Examples of glass bottle include, but are not limited to Type I, II and III borosilicate glass bottles. In an embodiment, the pharmaceutically acceptable container is a glass bottle, wherein the glass bottle may be an amber colored glass bottle or clear glass bottle. In preferred embodiment, the glass bottles will be available in 30, 60, 100, 120, 150, 250 & 500 mL fill volumes. In another embodiment the pharmaceutically acceptable container may be a plastic. Examples of plastic bottles include, but are not limited to, high-density polyethylene (HDPE), low density polyethylene (LDPE), PET (Polyethylene Terephthalate) and polypropylene (PP) bottles. In an embodiment, the pharmaceutically acceptable container is a plastic bottle, wherein the plastic bottle may be an amber color, white opaque or translucent plastic bottle. In preferred embodiment, the HDPE bottles will be available in 30, 60, 115, 120, 250 & 500 mL fill volumes.

The dosage forms may be provided in a package that consists of molded plastic or laminate that has indentations ("blisters") into which a dosage form, is placed, referred to herein as a "blister pack". A cover, typically a laminated material or foil, is used to seal to the molded part. A blister pack may or may not have pre-formed or molded parts.

Dissolution Testing:

In an embodiment, a stable pharmaceutical composition manufactured in the present application was tested for comparative dissolution by using USP apparatus-II (paddle) in dissolution media as described below. Preparation of dissolution media required for the studies was prepared as described below:

Dissolution media: 0.05 M Sodium Phosphate Buffer with 0.05% SLS (pH 6.8)

Preparation of 5N NaOH solution: Dissolve 20 g of Sodium hydroxide in 100 mL of purified water and sonicate to dissolve.

pH 6.8 Sodium phosphate buffer with 0.05% SLS: Dissolve 69 g of Sodium dihydrogen phosphate monohydrate in 10,000 mL of purified water and adjust the pH of the solution to 6.80±0.05 using 5N NaOH solution and mix well. Dissolve 5 g of Sodium lauryl sulfate into it and sonicate to dissolve. Degas the dissolution media under sonication.

Preparation of 0.1N HCl: Dissolve 2.1 ml of concentrated HCl with a pipette, and dilute to 250 ml with distilled water in a 250 ml-volumetric flask to obtain approximately 0.1N HCl.

In an embodiment, the present invention relates to stable soft-gelatin capsules of apixaban, suitable for oral administration, wherein the dissolution profile of the soft-gelatin capsules is comparable with the dissolution profile of commercially available immediate-release tablet formulation (Eliquis®) having National Drug Code Number 0003-0893-21, 0003-0893-31, 0003-0894-21, 0003-0894-31, 0003-0894-70, 0003-0894-74, and NDA Number 202155).

In an embodiment, the present invention relates to a pharmaceutical composition comprising: (a) apixaban; and (b) a pharmaceutically acceptable carrier system; wherein the composition provides an in-vitro release of not less than about 70 wt % of the apixaban, within 30 minutes of dissolution in 900 mL of a 0.05 M Sodium Phosphate Buffer with 0.05% SLS (pH 6.8) dissolution medium, measured using USP Apparatus II, at 75 RPM and 37° C.

In an embodiment, the present invention relates to a pharmaceutical composition comprising a fill material encapsulated in a capsule shell, wherein the fill material comprises: (a) apixaban; and (b) a pharmaceutically acceptable carrier system; wherein the capsule shell is optionally coated with a functional coating and wherein the composition provides an in-vitro release of not more than about 30 wt %, not more than about 35 wt %, not more than about 40 wt %, not more than about 45 wt %, not more than about 50 wt %, not more than about 55 wt %, or not more than about 60 wt % of the apixaban, within a time period selected from the group consisting of within 30 minutes, within 45 min, and within 60 min of dissolution in 900 mL or in 500 mL of a 0.05 M Sodium Phosphate Buffer without SLS or containing SLS in an amount selected from the group consisting of 0.05% SLS, 0.10% SLS, 0.15% SLS, 0.20% SLS, 0.25% SLS, 0.30% SLS, 0.40% SLS, 0.50% SLS, 0.70% SLS, and 1.0% SLS, (pH 6.8) dissolution medium, measured using USP Apparatus II, at 75 RPM and 37° C.

In an embodiment, the present invention relates to a pharmaceutical composition comprising a fill material encapsulated in a capsule shell, wherein the fill material comprises: (a) apixaban; and (b) a pharmaceutically acceptable carrier system; wherein the capsule shell is optionally coated with a functional coating and wherein the composition provides an in-vitro release of not more than about 50 wt % of the apixaban, within 60 min of dissolution in 900 mL of a 0.05 M Sodium Phosphate Buffer with 0.05% SLS, (pH 6.8) dissolution medium, measured using USP Apparatus II, at 75 RPM and 37° C.

In an embodiment, the present invention relates to a pharmaceutical composition comprising a fill material encapsulated in a capsule shell, wherein the fill material comprises: (a) apixaban; and (b) a pharmaceutically acceptable carrier system; wherein the capsule shell is optionally coated with a functional coating and wherein the composition provides an in-vitro release of not more than about 30 wt %, not more than about 35 wt %, not more than about 40 wt %, not more than about 45 wt %, not more than about 50 wt %, not more than about 55 wt %, or not more than about 60 wt % of the apixaban, within a time period selected from the group consisting of within 30 minutes, within 45 min, and within 60 min of dissolution in 900 mL or in 500 mL of a 0.1N HCl without SLS or or containing SLS in an amount selected from the group consisting of 0.05% SLS, 0.10% SLS, 0.15% SLS, 0.20% SLS, 0.25% SLS, 0.30% SLS, 0.40% SLS, 0.50% SLS, 0.70% SLS, and 1.0% SLS, (pH 1.2) dissolution medium, measured using USP Apparatus II, at 75 RPM and 37° C.

In an embodiment, the present invention relates to a pharmaceutical composition comprising a fill material encapsulated in a capsule shell, wherein the fill material comprises: (a) apixaban; and (b) a pharmaceutically acceptable carrier system; wherein the capsule shell is optionally coated with a functional coating and wherein the composition provides an in-vitro release of not more than about 50 wt % of the apixaban, within 60 min of dissolution in 900 mL of a 0.1N HCl with 0.05% SLS, (pH 1.2) dissolution medium, measured using USP Apparatus II, at 75 RPM and 37° C.

In an embodiment, the present invention relates to a pharmaceutical composition comprising a fill material encapsulated in a capsule shell, wherein the fill material comprises: (a) apixaban; and (b) a pharmaceutically acceptable carrier system; wherein the capsule shell is optionally coated with a functional coating and wherein the composition provides an in-vitro release of not less than about 60 wt %, not less than about 65 wt %, not less than about 70 wt %, not less than about 75 wt %, not less than about 80 wt %, or not less than about 90 wt %, of the apixaban, within 90 minutes or within 120 min, of dissolution in 900 mL or in 500 mL of a 0.05 M Sodium Phosphate Buffer without SLS or containing SLS in an amount selected from the group consisting of 0.05% SLS, 0.10% SLS, 0.15% SLS, 0.20% SLS, 0.25% SLS, 0.30% SLS, 0.40% SLS, 0.50% SLS, 0.70% SLS, and 1.0% SLS, (pH 6.8) dissolution medium, measured using USP Apparatus II, at 75 RPM and 37° C.

In an embodiment, the present invention relates to a pharmaceutical composition comprising a fill material encapsulated in a capsule shell, wherein the fill material comprises: (a) apixaban; and (b) a pharmaceutically acceptable carrier system; wherein the capsule shell is optionally coated with a functional coating and wherein the composition provides an in-vitro release of not less than about 70 wt % of the apixaban, within 120 min, of dissolution in 900 mL of a 0.05 M Sodium Phosphate Buffer with 0.05% SLS (pH 6.8) dissolution medium, measured using USP Apparatus II, at 75 RPM and 37° C.

In an embodiment, the present invention relates to a pharmaceutical composition comprising a fill material encapsulated in a capsule shell, wherein the fill material comprises: (a) apixaban; and (b) a pharmaceutically acceptable carrier system; wherein the capsule shell is optionally coated with a functional coating and wherein the composition provides an in-vitro release of not less than about 60 wt %, not less than about 65 wt %, not less than about 70 wt %, not less than about 75 wt %, not less than about 80 wt %, or not less than about 90 wt %, of the apixaban, within 90 minutes or within 120 min, of dissolution in 900 mL or in 500 ml of a 0.1N HCl without SLS or containing SLS in an amount selected from the group consisting of 0.05% SLS, 0.10% SLS, 0.15% SLS, 0.20% SLS, 0.25% SLS, 0.30% SLS, 0.40% SLS, 0.50% SLS, 0.70% SLS, and 1.0% SLS, (pH 1.2) dissolution medium, measured using USP Apparatus II, at 75 RPM and 37° C.

In an embodiment, the present invention relates to a pharmaceutical composition comprising a fill material encapsulated in a capsule shell, wherein the fill material comprises: (a) apixaban; and (b) a pharmaceutically acceptable carrier system; wherein the capsule shell is optionally coated with a functional coating and wherein the composition provides an in-vitro release of not less than about 70 wt % of the apixaban, within 120 min, of dissolution in 900 mL of a 0.1N HCl with 0.05% SLS (pH 6.8) dissolution medium, measured using USP Apparatus II, at 75 RPM and 37° C.

Bioequivalence:

In an embodiment, the inventive pharmaceutical composition as described herein upon oral administration in fasting condition exhibits bioequivalence to a commercially available reference drug product (such as Eliquis®) having the same dosage amount, in the fasting condition, and wherein said bioequivalence is established by at least one of: (i) a confidence interval for geometric mean $AUC_{0-t}$ between about 80% and about 125%; (ii) a confidence interval for geometric mean $AUC_{0\text{-}infinity}$ between about 80% and about 125%; (iii) a confidence interval for geometric mean $C_{max}$ between about 80% and about 125% or combination thereof.

In an embodiment, the inventive pharmaceutical composition as described herein upon oral administration in fed condition exhibits bioequivalence to a commercially available reference drug product (such as Eliquis®) having the same dosage amount, in the fed condition, and wherein said bioequivalence is established by at least one of: (i) a confidence interval for geometric mean $AUC_{0-t}$ between about 80% and about 125%; (ii) a confidence interval for geometric mean $AUC_{0\text{-}infinity}$ between about 80% and about 125%; (iii) a confidence interval for geometric mean $C_{max}$ between about 80% and about 125% or combination thereof.

In an embodiment, an immediate-release inventive pharmaceutical composition as described herein upon oral administration is provided comprising a fill material encapsulated in a capsule shell, wherein the fill material comprises apixaban and a pharmaceutically acceptable carrier system comprising at least one of a solubilizing agent, a crystallization inhibitor, a stabilizer, and a solvent; wherein fill material is in the form of a liquid; wherein apixaban is uniformly solubilized in the pharmaceutically acceptable carrier system; and wherein the capsule shell is a gelatin capsule coated with a functional coating, wherein the said composition upon administration exhibits a bioequivalence to a commercially available reference drug product approved by U.S. Food and Drug Administration under New Drug Application Number 202155 and National Drug Code Number 0003-0893 and 0003-0894; and wherein the said bioequivalence is established by at least one of: (i) a confidence interval for mean $AUC_{0-t}$ between about 80% and about 125%; (ii) a confidence interval for mean $AUC_{0-infinity}$ between about 80% and about 125%; (iii) a confidence interval for mean $C_{max}$ between about 80% and about 125%, following administration in human subjects under fasting as well as fed condition.

In an embodiment, an immediate-release inventive pharmaceutical composition as described herein upon oral administration is provided comprising a fill material encapsulated in a capsule shell, wherein the fill material comprises apixaban and a pharmaceutically acceptable carrier system comprising at least one of a solubilizing agent, a crystallization inhibitor, a stabilizer, and a solvent; wherein fill material is in the form of a liquid; wherein apixaban is uniformly solubilized in the pharmaceutically acceptable carrier system; and wherein the capsule shell is a gelatin capsule coated with a functional coating, wherein the said pharmaceutical composition provides a release of the apixaban bioequivalent to the same dose of apixaban in immediate release tablet form, wherein the said bioequivalence is established by at least one of: (i) a confidence interval for mean $AUC_{0-t}$ between about 80% and about 125%; (ii) a confidence interval for mean $AUC_{0-infinity}$ between about 80% and about 125%; (iii) a confidence interval for mean $C_{max}$ between about 80% and about 125%, following administration in human subjects under fasting as well as fed condition.

Stability:

As used herein, the term "stable" is defined as no more than about 10% loss of apixaban under typical commercial storage conditions. In certain embodiments, the compositions of the present invention, wherein the loss of apixaban is no more than about 5% loss, no more than about 4% loss, no more than about 3% loss, no more than about 2% loss, no more than about 1% loss, under typical commercial storage conditions. The composition retains at least about 90% of the potency of apixaban, as determined by HPLC at a wavelength of 278 nm, after storing the composition at 40° C./75% RH or at 25° C./60% RH or at 40° C./25% RH for at least 3 months, at least 6 months, at least 9 months, at least 12 months, at least 15 months, at least 18 months, at least 21 months, at least 24 months, at least 30 months and at least 36 months. In certain aspects, the term "stable" refers to chemical stability, wherein not more than about 2% w/w of total impurities, preferably not more than about 1.5% w/w of total impurities, more preferably not more than about 1% w/w of total impurities are formed on storage at 40° C./75% RH or at 25° C./40% RH or at 40° C./25% RH for at least 3 months, at least 6 months, at least 9 months, at least 12 months, at least 15 months, at least 18 months, at least 21 months, at least 24 months, at least 30 months and at least 36 months.

In an embodiment, the present invention relates to stable pharmaceutical compositions suitable for oral administration comprising apixaban solubilized in a pharmaceutically acceptable carrier system, wherein apixaban does not precipitate or crystallize from the composition for at least 1 month, for at least 2 months, for at least 3 months, for at least 6 months, for at least 9 months, for at least 12 months, for at least 18 months, for at least 24 months when stored at room temperature.

In an embodiment, the present invention relates to stable pharmaceutical compositions suitable for oral administration comprising apixaban solubilized in a pharmaceutically acceptable carrier system, wherein apixaban does not precipitate or crystallize from the composition for at least 1 month, for at least 2 months, for at least 3 months, for at least 6 months upon storage at 40° C./75% RH or at 40° C./25% RH and for at least 1 month, for at least 3 months, for at least 6 months, for at least 9 months, for at least 12 months, for at least 18 months, for at least 24 months upon storage at 25° C./60% RH.

In an embodiment, the present invention provides stable pharmaceutical compositions suitable for oral administration comprising apixaban solubilized in at least one solubilizing agent; and (iii) optionally one or more pharmaceutically acceptable excipients, wherein the composition is stable for at least 1 month, for at least 2 months, for at least 3 months, for at least 6 months upon storage at 40° C./75% RH or at 40° C./25% RH and for at least 1 month, for at least 3 months, for at least 6 months, for at least 9 months, for at least 12 months, for at least 18 months, for at least 24 months upon storage at 25° C./60% RH.

In one embodiment, the present invention provides stable pharmaceutical compositions suitable for oral administration wherein apixaban is solubilized in a pharmaceutically acceptable carrier system wherein the pharmaceutically acceptable carrier system comprises (i) at least one solubilizing agent; and (ii) optionally one or more pharmaceutically acceptable excipients, wherein the composition is stable for at least 1 month, for at least 2 months, for at least 3 months, for at least 6 months upon storage at 40° C./75% RH or at 40° C./25% RH and for at least 1 month, for at least 3 months, for at least 6 months, for at least 9 months, for at least 12 months, for at least 18 months, for at least 24 months upon storage at 25° C./60% RH.

In another embodiment, the present invention provides stable pharmaceutical compositions suitable for oral administration wherein apixaban is dispersed in a pharmaceutically acceptable carrier system wherein the pharmaceutically acceptable carrier system comprises (i) at least one solubilizing agent; and (ii) optionally one or more pharmaceutically acceptable excipients, wherein the composition is stable for at least 1 month, for at least 2 months, for at least 3 months, for at least 6 months upon storage at 40° C./75% RH or at 40° C./25% RH, and for at least 1 month, for at least 3 months, for at least 6 months, for at least 9 months, for at least 12 months, for at least 18 months, for at least 24 months upon storage at 25° C./60% RH.

Apixaban has known as well as unknown impurities. In particular, acid impurity, amino acid impurity, dehydro impurity, chloro impurity, ester impurity and methyl ester impurity were monitored.

TABLE 2

The potential impurities for Apixaban

| S. No | Impurity Name | Type | Structure | Chemical Name |
|---|---|---|---|---|
| 1. | Acid Impurity | Process/ Degradation | 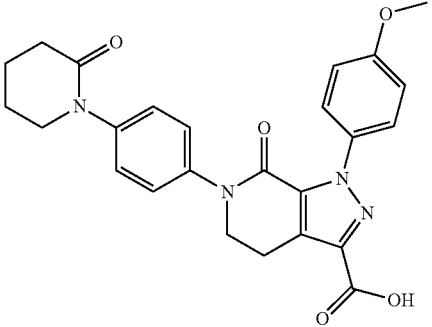 [SMILES: COc1ccc(-n2nc(C(=O)O)c3c2C(=O)N(c2ccc(N4CCCCC4=O)cc2)CC3)cc1] | 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid |
| 2. | Amino Acid Impurity | Process/ Degradation | 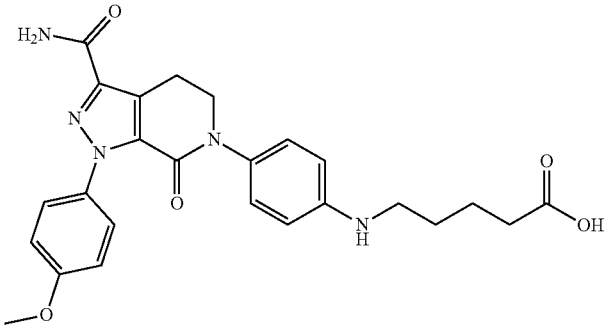 [SMILES: COc1ccc(-n2nc(C(N)=O)c3c2C(=O)N(c2ccc(NCCCCC(=O)O)cc2)CC3)cc1] | 5-((4-(3-Carbamoyl-1-(4-methoxy phenyl)-7-oxo-1,4,5,7-tetrahydro-6H-pyrazolo[3,4-c]pyridin-6-yl)phenyl)amino)pentanoic acid |
| 3. | Dehydro Impurity | Process/ Degradation | 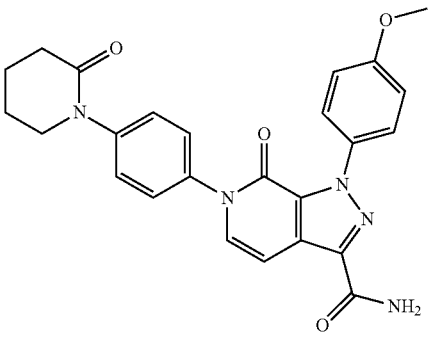 [SMILES: COc1ccc(-n2nc(C(N)=O)c3ccn(-c4ccc(N5CCCCC5=O)cc4)c(=O)c32)cc1] | 1-(4-Methoxyphenyl)-7-oxo-6-(4-(2-oxopiperidin-1-yl)phenyl)-6,7-dihydro-1H-pyrazolo[3,4-c]pyridine-3-carboxamide |
| 4. | Chloro Impurity | Process | 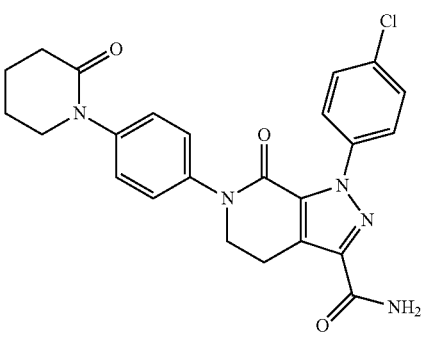 [SMILES: NC(=O)c1nn(-c2ccc(Cl)cc2)c2c1CCN(c1ccc(N3CCCCC3=O)cc1)C2=O] | 1-(4-Chlorophenyl)-7-oxo-6-(4-(2-oxopiperidin-1-yl)phenyl)-4,5,6,7-tetrahydro-1H-pyrazolo[3,4-c]pyridine-3-carboxamide |

TABLE 2-continued

The potential impurities for Apixaban

| S. No | Impurity Name | Type | Structure | Chemical Name |
|---|---|---|---|---|
| 5. | Methyl Ester Impurity | Process | 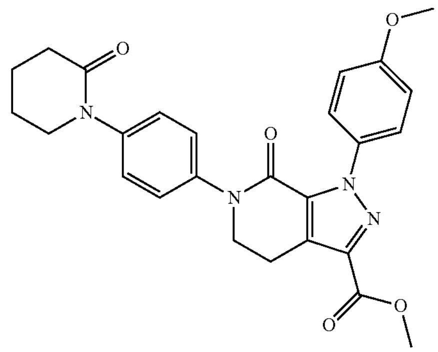 [SMILES: COC(=O)c1nn(-c2ccc(OC)cc2)c2c1CCN(c1ccc(N3CCCCC3=O)cc1)C2=O] | methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate |
| 6. | Ester Impurity | Process | 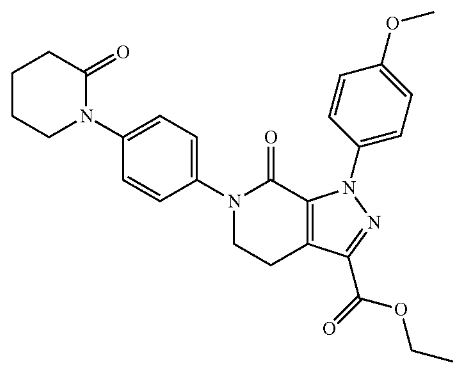 [SMILES: CCOC(=O)c1nn(-c2ccc(OC)cc2)c2c1CCN(c1ccc(N3CCCCC3=O)cc1)C2=O] | ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate |

In an embodiment, the present invention provides stable pharmaceutical compositions suitable for oral administration comprising apixaban solubilized in a pharmaceutically acceptable carrier system wherein the pharmaceutically acceptable carrier system comprises (i) at least one solubilizing agent; and (ii) optionally one or more pharmaceutically acceptable excipients, wherein the level of total impurities in the composition is less than about 5% w/w, preferably less than about 3% w/w, more preferably less than about 1% w/w, most preferably less than about 0.5% w/w as determined by HPLC at a wavelength of 270 nm.

In another embodiment, the present invention provides stable pharmaceutical compositions suitable for oral administration comprising apixaban dispersed in a pharmaceutically acceptable carrier system wherein the pharmaceutically acceptable carrier system comprises (i) at least one solubilizing agent; and (ii) optionally one or more pharmaceutically acceptable excipients, wherein the level of total impurities in the composition is less than about 5% w/w, preferably less than about 3% w/w, more preferably less than about 1% w/w, most preferably less than about 0.5% w/w as determined by HPLC at a wavelength of 270 nm.

In another embodiment, the level of any unknown impurities in the inventive composition resulting from the degradation of apixaban is less than about 5% (w/w), less than about 3% (w/w), less than about 1% (w/w), less than about 0.5% (w/w), less than about 0.15% (w/w) or less than about 0.1% (w/w) as determined by HPLC at a wavelength of 270 nm.

In yet another embodiment, the level of known impurities in the inventive composition resulting from the degradation of apixaban is less than about 5% (w/w), or less than about 3% (w/w), or less than about 1% (w/w), or less than about 0.5% (w/w), or less than about 0.15% (w/w) or less than about 0.1% (w/w) as determined by HPLC at a wavelength of 270 nm.

Analysis of samples withdrawn during chemical analysis of apixaban

The samples withdrawn were analyzed for drug content using the following illustrative HPLC procedure. The materials and general conditions are listed below:

TABLE 3

| Chromatographic conditions (Drug content analysis) | |
|---|---|
| Chromatographic Mode | HPLC system equipped with UV/PDA detector |
| Column | Poroshell 120, SB-C18, 4.6 × 150 mm, 2.7 μm; PN: 683975-902 or equivalent |
| Wavelength | Apixaban: 278 nm |
| Flow rate | 0.8 mL/minute |
| Injection volume | 15 μL |
| Column temperature | 30° C. |
| Sample temperature | 25° C. |
| Run time | 30 minutes |
| Mobile Phase A | Buffer (pH2.5) solution and acetonitrile in the ratio of 70:30 (% v/v). |
| Mobile Phase B | Buffer (pH2.5) solution and acetonitrile in the ratio of 30:70 (% v/v). |

TABLE 3-continued

Chromatographic conditions (Drug content analysis)

| Mode of Elution | Time | Gradient | |
|---|---|---|---|
| | | Mobile Phase-A (%) | Mobile Phase-B (%) |
| | 0 | 100 | 0 |
| | 13 | 100 | 0 |
| | 20 | 0 | 100 |
| | 24 | 0 | 100 |
| | 25 | 100 | 0 |
| | 30 | 100 | 0 |

The samples withdrawn were analyzed for related substances using the following illustrative HPLC procedure. The materials and general conditions are listed below:

TABLE 4

Chromatographic conditions (Related substance analysis)

| | |
|---|---|
| Chromatographic Mode | HPLC system equipped with UV/PDA detector |
| Column | Zorbax SB Phenyl 250 × 4.6 mm, 5μ, PN: 880975-912 or equivalent |
| Wavelength | 270 nm |
| Flow rate | 1.0 mL/minute |
| Injection volume | 40 μL |
| Column temperature | 40° C. |
| Sample temperature | 25° C. |
| Run time | 65 minutes |
| Mobile Phase A | Buffer (pH5.5) solution and acetonitrile in the ratio of 90:10 (% v/v). |
| Mobile Phase B | Buffer (pH5.5) solution and acetonitrile in the ratio of 10:90 (% v/v). |

| Mode of Elution | Time | Gradient | |
|---|---|---|---|
| | | Mobile Phase-A (%) | Mobile Phase-B (%) |
| | 0 | 90 | 10 |
| | 15 | 90 | 10 |
| | 32 | 70 | 30 |
| | 53 | 55 | 45 |
| | 58 | 55 | 45 |
| | 59 | 90 | 10 |
| | 65 | 90 | 10 |

The samples withdrawn were analyzed for dissolution testing using the following illustrative HPLC procedure. The materials and general conditions are listed below:

TABLE 5

Chromatographic conditions (Dissolution testing)

| | |
|---|---|
| Chromatographic Mode | HPLC system equipped with UV/PDA detector |
| Column | Zorbax Eclipse XDB C18, 4.6 × 150 mm, 5 μm; PN: 993967-902 or equivalent |
| Wavelength | 278 nm |
| Flow rate | 1.0 mL/minute |
| Injection volume | 10 μL |
| Column temperature | 40° C. |
| Sample temperature | 25° C. |
| Run time | 10 minutes |
| Mobile Phase | Buffer (pH5.5) solution, Methanol, and acetonitrile in the ratio of 50:35:15 (% v/v/v). |
| Mode of Elution | Isocratic |

EXAMPLES

The following examples are exemplary and not intended to be limiting. The above disclosure provides many different embodiments for implementing the features of the invention, and the following examples describe certain illustrative embodiments. It will be appreciated that other modifications and methods known to one of ordinary skill in the art can also be applied to the following experimental procedures, without departing from the scope of the invention.

Example 1

Apixaban compositions are set forth in Table 6.

TABLE 6

| S. No. | Ingredients | Composition (mg/cap) | | |
|---|---|---|---|---|
| | | A | B | C |
| 1 | Apixaban | 5.0 | 5.0 | 5.0 |
| 2 | Polyethylene Glycol-200 | 100.0 | 50.0 | — |
| 3 | Polyethylene Glycol-400 | 550.0 | 520.0 | 520.0 |
| 4 | Propylene Glycol | 200.0 | 200.0 | 200.0 |
| 5 | Triacetin | 50.0 | 25.0 | 25.0 |
| | Total capsule content | 905.0 | 800.0 | 750.0 |

Manufacturing Procedure of Compositions A, B and C:

Polyethylene glycol and triacetin were mixed together. Weighed quantity of apixaban was added to the resulting mixture under stirring at a temperature of 45° C.±5° C. Propylene glycol was added at a temperature of about 75° C. The final compositions were stored at room temperature in clear glass vials and checked for chemical and physical stability.

TABLE 7

Stability data

| | Composition | | | | | |
|---|---|---|---|---|---|---|
| | A | | B | | C | |
| Stability condition | Initial | 6 M RT | Initial | 6 M RT | Initial | 30 D 60° C. |
| Description | Clear Solution | | Clear Solution | | Clear Solution | |
| Assay | 97.3 | 97.5 | 96.4 | 94.5 | 97.1 | 97.9 |
| Related Substances | | | % Impurity | | | |
| Acid Impurity | ND | ND | ND | ND | ND | ND |
| Amino acid Impurity | ND | 0.140 | ND | 0.010 | ND | 0.09 |
| Dehydro Impurity | 0.07 | 0.100 | 0.05 | 0.050 | 0.049 | 0.17 |
| Single max Unknown Imp | 0.095 | 0.090 | 0.06 | 0.08 | 0.059 | 0.120 |
| Total impurities | 0.377 | 0.780 | 0.24 | 0.24 | 0.245 | 0.76 |

RT: Room Temperature
D: Days

Compositions A and B showed very good chemical and stability even upon storage at room temperature for a period of 6 months. Composition C also showed clear physical appearance upon storage for as long as 6 months.

Example 2

Apixaban compositions are set forth in Table 8.

TABLE 8

| S. No. | Ingredients | Composition (mg/cap) | | | | |
|---|---|---|---|---|---|---|
| | | D | E | F | G | H |
| 1 | Apixaban | 5.0 | 5.0 | 5.0 | 5.0 | 5.0 |
| 2 | Polyethylene Glycol-400 | 187.0 | 189.0 | 189.0 | 540.0 | 400.0 |
| 3 | Propylene Glycol | 228.0 | 231.0 | 231.0 | — | 110.0 |
| 4 | Triacetin | 25.0 | 25.0 | 25.0 | — | 25.0 |
| 5 | Sodium lauryl sulphate | — | 5.0 | — | — | — |
| 6 | Polyvinylpyrrolidone | 10.0 | 5.0 | 10.0 | 5.0 | 10.0 |
| 7 | Glycerine | 40.0 | 40.0 | 40.0 | — | — |
| 8 | Polyoxyl 40 hydrogenated castor oil | 5.0 | — | — | — | — |
| | Total capsule content | 500.0 | 500.0 | 500.0 | 550.0 | 550.0 |

Manufacturing Procedure of Compositions D to H:

Polyethylene glycol and triacetin were mixed together. Polyvinylpyrrolidone was added to the resulting mixture followed by other surfactants or antioxidants or fillers. Upon complete dissolution of polyvinylpyrrolidone, the weighed quantity of apixaban was added to the resulting mixture under stirring at a temperature of 45° C.±5° C. Propylene glycol was added at a temperature of about 75° C. The final compositions were stored at room temperature in clear glass vials and checked for chemical and physical stability. Compositions E and F were encapsulated into soft gelatin capsules and checked for stability.

TABLE 9

Stability data Composition E

| Condition | Initial | 25° C./ 60% RH | 40° C./ 75% RH | 25° C./ 60% RH | 40° C./ 75% RH |
|---|---|---|---|---|---|
| Time point | Initial | 1 month | | | |
| Pack | | HDPE bottle | | Blister pack | |
| Assay | 96.5 | 99.6 | 96.9 | NP | NP |
| Related substances | | % impurity | | | |
| Acid impurity | ND | ND | ND | ND | ND |
| Amino acid impurity | 0 | ND | ND | ND | ND |
| Dehydro impurity | 0.05 | 0.05 | 0.06 | 0.06 | 0.06 |
| Single max unknown impurity | 0.08 | 0.07 | 0.07 | 0.08 | 0.07 |
| Total Impurities | 0.22 | 0.18 | 0.18 | 0.2 | 0.2 |

NP: Not performed;
ND: Not Detected

TABLE 10

Stability data Composition F

| Condition | Initial | 25° C./ 60% RH | 40° C./ 75% RH | 25° C./ 60% RH | 40° C./ 75% RH |
|---|---|---|---|---|---|
| Time point | Initial | 1 month | | | |
| Pack | | HDPE | | Blister | |
| Assay | 98.7 | 99.6 | 95.6 | NP | NP |
| Related substances | | % impurity | | | |
| Acid impurity | ND | ND | ND | ND | ND |

TABLE 10-continued

Stability data Composition F

| Condition | Initial | 25° C./ 60% RH | 40° C./ 75% RH | 25° C./ 60% RH | 40° C./ 75% RH |
|---|---|---|---|---|---|
| Amino acid impurity | ND | ND | ND | ND | ND |
| Dehydro impurity | 0.05 | 0.06 | 0.07 | 0.06 | 0.07 |
| Single max unknown impurity | 0.07 | 0.07 | 0.08 | 0.09 | 0.08 |
| Total Impurities | 0.22 | 0.19 | 0.21 | 0.21 | 0.21 |

Compositions E and F showed very good chemical and physical stability even upon storage at 25° C./60% RH and 40° C./75% for a period of 1 month. Compositions D, G and H also showed clear physical appearance upon storage for at least 1 month.

Example 3

Apixaban compositions are set forth in Table 11.

TABLE 11

| S. No. | Ingredients | Composition (mg/cap) | |
|---|---|---|---|
| | | I | J |
| 1 | Apixaban | 5.0 | 5.0 |
| 2 | Polyethylene Glycol-400 | 158.62 | 129.25 |
| 3 | Polyethylene Glycol-3350 | 52.88 | 129.25 |
| 4 | Propylene Glycol | 258.50 | 211.50 |
| 5 | Triacetin | 25.00 | 25.00 |
| | Total capsule content | 500.0 | 500.0 |

Manufacturing Procedure of Compositions I and J:

Polyethylene glycol and triacetin were mixed together. Weighed quantity of apixaban was added to the resulting mixture under stirring at a temperature of 45° C.±5° C. Propylene glycol was added at a temperature of about 75° C. The final compositions I and J were encapsulated into soft gelatin capsules and checked for stability.

TABLE 12

| Composition | I | J |
|---|---|---|
| Condition | Initial | Initial |
| Related substances | % impurity | |
| Acid impurity | ND | ND |
| Amino acid impurity | ND | ND |
| Dehydro impurity | 0.05 | 0.06 |
| Single max unknown impurity | 0.07 | 0.06 |
| Total Impurities | 0.19 | 0.17 |

Compositions I and J showed very good chemical and physical properties.

Example 4

Dissolution profiles of Eliquis® 5 mg tablets and 'composition F' in 0.05 M Sodium Phosphate Buffer with 0.05% SLS (pH 6.8) dissolution media were compared by using USP apparatus II (paddle); 900 mL of phosphate buffer of pH 6.8 dissolution media for 75 minutes and stirred at 75 rpm. Samples were withdrawn at 10, 20, 30, 45, 60 and 75 minutes and analyzed using HPLC system.

TABLE 13

Dissolution data

| Product | Eliquis® Batch No. FE8987 | Composition F |
|---|---|---|
| Media: | 0.05M Sodium Phosphate Buffer with 0.05% SLS (pH 6.8) | |
| Volume: | 900 mL | |
| Apparatus: | Paddles (Type-2) | |

| Sr. No. | Time points (min) | % Drug Release | |
|---|---|---|---|
| 1 | 5 | 27 | 0 |
| 2 | 10 | 67 | 74 |
| 3 | 15 | 79 | 90 |
| 4 | 20 | 83 | 91 |
| 5 | 30 | 88 | 93 |
| 6 | 45 | 92 | 95 |
| 7 | 60 | 94 | 96 |
| 8 | 75 | 94 | 96 |

Both the formulations (Eliquis® 5 mg tablets and composition F) show no less than 90% release at the end of 45 min.

Example 5

TABLE 14

Composition K

| S. No | Ingredients | Functional Category | F051 mg/unit |
|---|---|---|---|
| | Fill material# | | |
| 1 | Apixaban | Active | 5 |
| 2 | Polyethylene Glycol | Solubilizer | 500 |
| 3 | Propylene Glycol | Solubilizer | 60 |
| 4 | Triacetin | Solubilizer | 25 |
| 5 | Polyvinyl pyrrolidone | Crystal Inhibitor | 10 |
| | Fill Weight | | 600 |
| | Capsule shell composition | | |
| 6 | Gelatin | Shell Former | 44% |
| 8 | Sorbitol | Plasticizer | 10% |
| 9 | Glycerin | Plasticizer | 10% |
| 10 | Purified Water | Solvent | 36% |

* % based on total weight of the capsule shell composition
QS Quantity sufficient
Appearance of fill material: clear solution

TABLE 15

Initial Dissolution Data

| Media: | pH 6.8 Phosphate buffer + 0.05% SLS-75 RPM |
| Volume: | 900 mL |
| Apparatus: | Paddles (Type-II) |

| | Eliquis® Tablets (Batch No: 1876129) | Apixaban Soft Gelatin Capsule (Composition K) |
|---|---|---|
| | % Drug Release | |
| Time in Min | Average | Average |
| 0 | 0 | 0 |
| 5 | 28 | 4 |
| 10 | 65 | 65 |
| 15 | 84 | 98 |
| 20 | 89 | 99 |
| 30 | 93 | 99 |

TABLE 15-continued

Initial Dissolution Data

| 45 | 96 | 100 |
| 60 | 96 | 100 |
| 75 | 97 | 100 |

Both the formulations (Eliquis® 5 mg tablets and composition K) show no less than 90% release at the end of 30 min.

TABLE 16

Stability data

| | | Composition K | | | |
|---|---|---|---|---|---|
| | | 40° C./ 75% RH 6 M | 25° C./ 60% RH 6 M | 40° C./ 75% RH 6 M | 25° C./ 60% RH 6 M |
| Test | Initial | HDPE | HDPE | Blister | Blister |
| Assay | 98.6 | 101.1 | 100.1 | 99.8 | 100.6 |
| Appearance of fill material | | Clear Solution | | | |
| Impurity profile | | | | | |
| Acid Impurity | ND | 0.01 | 0 | 0.01 | 0 |
| Amino Acid Impurity | ND | 0.01 | 0.01 | 0.01 | 0.01 |
| Dehydro impurity | 0.05 | 0.05 | 0.05 | 0.05 | 0.05 |
| Single max unknown impurity | 0.08 | 0.07 | 0.08 | 0.06 | 0.07 |
| Total Impurities | 0.19 | 0.4 | 0.29 | 0.34 | 0.26 |

TABLE 17

Dissolution Data upon stability

| Media: | pH 6.8 Phosphate buffer + 0.05% SLS-75 RPM |
| Volume: | 900 mL |
| Apparatus: | Paddles (Type-II) |
| Formulation | Apixaban Soft Gelatin Capsule (Composition K) |

| | 25° C./60% RH 6 months HDPE Bottle | 25° C./60% RH 6 months Blister pack |
|---|---|---|
| | % Drug Release | |
| Time in Min | Average | Average |
| 0 | 0 | 0 |
| 5 | 2 | 1 |
| 10 | 17 | 12 |
| 15 | 22 | 19 |
| 20 | 57 | 42 |
| 30 | 92 | 79 |
| 45 | 97 | 96 |
| 60 | 97 | 95 |
| Recovery | 98 | 96 |

Composition K show no less than 90% release at the end of 45 min upon stability at 25° C./60% RH until six months.

Example 6

TABLE 18

Composition L

| Ingredients | Functionality | Composition L mg/unit |
|---|---|---|
| Fill Material# | | |
| Apixaban | Active | 5 |
| Polyethylene Glycol | Solubilizing agent | 500 |
| Propylene Glycol | Solubilizing agent | 60 |
| Triacetin | Solubilizing agent | 25 |
| Polyvinyl pyrrolidone | Crystallization inhibitor | 10 |
| Fill Weight | | 600 |
| Capsule shell composition | | |
| Gelatin | Shell Forming agent | *44% |
| Sorbitol | Plasticizer | *10% |
| Glycerine | Plasticizer | *10% |
| Purified Water | Vehicle | *36% |
| Core Capsule Weight | | 908 mg |
| Seal coating composition | | |
| Hydroxypropyl methylcellulose | Coating Material | 3% of the core capsule weight |
| Purified Water | Vehicle | QS |
| Seal Capsule Weight | | 935.24 mg |
| Functional coating | | |
| Acrylic acid-methacrylic acid-based polymer (Eudragit L30 D55) | Release rate controlling Polymer | 8% of core capsule weight |
| Talc | Anti-tacking Agent | 50% of release rate controlling polymer |
| Triethyl citrate | Plasticizer | 10% of release rate controlling polymer |
| Purified water | Vehicle | Qs |
| Coated Capsule Total | | 1010.06 mg |

*% based on total weight of the capsule shell composition
QS Quantity sufficient
Appearance of fill material: clear solution A brief manufacturing process flow chart is as described in FIG. 1.

TABLE 19

Initial Dissolution Data

| Media: | pH 6.8 Phosphate buffer + 0.05% SLS-75 RPM |
| Volume: | 900 mL |
| Apparatus: | Paddles (Type-II) |

| | Eliquis ® Tablets (Batch No: 1876129) | Apixaban Soft Gelatin Capsule (Composition L) |
|---|---|---|
| | % Drug Release | |
| Time in Min | Average | Average |
| 0 | 0 | 0 |
| 5 | 28 | 1 |
| 10 | 65 | 5 |
| 15 | 84 | 10 |
| 20 | 89 | 18 |
| 30 | 93 | 84 |
| 45 | 96 | 96 |
| 60 | 96 | 95 |
| 75 | 97 | 96 |

Both the formulations (Eliquis® 5 mg tablets and composition L) show no less than 90% release at the end of 45 min.

Example 7

TABLE 20

Composition M

| Ingredients | Category | mg/unit |
|---|---|---|
| Fill material# | | |
| Apixaban | Active | 5 |
| Polyethylene Glycol-400 | Solubilizing agent | 500 |
| Propylene Glycol USP | Solubilizing agent | 60 |
| Triacetin, USP | Plasticizer | 25 |
| Polyvinyl pyrrolidone | Crystallization inhibitor | 10 |
| Fill weight | | 600 |
| Capsule shell | | |
| Gelatin | Film forming polymer | *44% |
| Sorbitol | Plasticizer | *10% |
| Glycerin | | *10% |
| Purified Water | solvent | *36% |
| Core Capsule Total | | NA |
| Seal coal | | |
| Hydroxypropyl methylcellulose | Seal coating polymer | 3% of core capsule weight |
| Purified Water | solvent | QS |
| Seal Coated Capsule Total | | 932.4 |
| Functional coat | | |
| Ethyl Cellulose | Rate controlling polymer | 15.89 |
| HPMC E3 | Polymer or pore forming agent | 35.76 |
| Polyethylene glycol | Plasticizer | 5.16 |
| Talc | Anti tacking agent | 10.30 |
| Lactose monohydrate | Pore forming agent | 27.81 |
| Isopropyl Alcohol | Solvent | QS |
| Purified Water | Solvent | QS |
| Coated Capsule Total | | 1027.32 |

*% based on total weight of the capsule shell composition
QS Quantity sufficient
Appearance of fill material: clear solution A brief manufacturing process flow chart is as described in FIG. 1.

TABLE 21

Initial Dissolution data

| Media: | pH 6.8 Phosphate buffer + 0.05% SLS-75 RPM |
| Volume: | 900 mL |
| Apparatus: | Paddles (Type-II) |

| Type Batch No | Apixaban Soft Gelatin Capsule Composition M |
|---|---|
| Time in Min | % Drug Release |
| 0 | 0 |
| 15 | 4 |
| 30 | 21 |
| 45 | 74 |
| 60 | 87 |
| 90 | 96 |

TABLE 21-continued

| Initial Dissolution data | |
|---|---|
| 120 | 95 |
| Recovery | 94 |

Composition M show no less than 90% release at the end of 90 min.

Example 8

TABLE 22

| Composition N | | |
|---|---|---|
| Ingredients | Functionality | Composition N mg/unit |
| Fill Material# | | |
| Apixaban | Active | 5 |
| Polyethylene Glycol | Solubilizing agent | 500 |
| Propylene Glycol | Solubilizing agent | 60 |
| Triacetin | Solubilizing agent | 25 |
| Polyvinyl pyrrolidone | Crystallization inhibitor | 10 |
| Fill Weight | | 600 |
| Capsule shell composition | | |
| Gelatin | Shell Forming agent | *44% |
| Sorbitol | Plasticizer | *10% |

TABLE 22-continued

| Composition N | | |
|---|---|---|
| Ingredients | Functionality | Composition N mg/unit |
| Glycerine | Plasticizer | *10% |
| Purified Water | Vehicle | *36% |
| Core Capsule Weight | | |
| Seal coating composition | | |
| Hydroxypropyl methylcellulose | Coating Material | 3% of the core capsule weight |
| Purified Water | Vehicle | QS |
| Seal Capsule Weight | | 930.60 mg |
| Functional coating | | |
| Acrylic acid-methacrylic acid-based polymer (Eudragit RL 30D) | Release rate controlling Polymer | 53.18 |
| Talc | Anti-tacking Agent | 21.27 |
| Polyethylene glycol | Plasticizer | 5.32 |
| Lactose monohydrate | Pore former | 13.30 |
| Purified water | Vehicle | QS |
| Coated Capsule Total | | 1023.70 mg |

*% based on total weight of the capsule shell composition
QS Quantity sufficient
Appearance of fill material: clear solution A brief manufacturing process flow chart is as described in FIG. 1.

Example 9

TABLE 23

| | | Composition O | | | |
|---|---|---|---|---|---|
| | | 2.5 mg | | 5 mg | |
| Ingredients | Functional Category | Quantity/Unit (mg/capsule) | % w/w (Total capsule) | Quantity/Unit (mg/capsule) | % w/w (Total Capsule) |
| Apixaban | Active Pharmaceutical Ingredient | 2.5 mg | 0.260 | 5.0 mg | 0.519 |
| Polyethylene Glycol | Solubilizer | 502.5 mg | 52.170 | 500.0 mg | 52.911 |
| Propylene Glycol | Solubilizer | 60.0 mg | 6.229 | 60.0 mg | 6.265 |
| Triacetin | Solubilizer | 25 mg | 2.596 | 25.0 mg | 2.610 |
| Polyvinyl pyrrolidone | Crystal inhibitor | 10.0 mg | 1.038 | 10.0 mg | 1.044 |
| Sub Total (Fill material#) | | 600.0 mg | — | 600.0 mg | — |
| Gelatin | Shell Former | 210.00 mg | 21.803 | 210.00 mg | 21.803 |
| Glycerin | Plasticizer | 30.00 mg | 3.115 | 30.00 mg | 3.115 |
| Sorbitol Solution | Plasticizer | 30.00 mg | 3.115 | 30.00 mg | 3.115 |
| Purified Water | Vehicle of Shell | 30.00 mg | 3.115 | 30.00 mg | 3.115 |
| Sub Total (Shell) | | 300.00 mg | — | 300.00 mg | — |
| Ammonio Methacrylate Copolymer Type A ® (Eudragit RL30D) | Rate-Controlling polymer | 21.72 mg | 2.255 | 21.72 mg | 2.255 |
| Hydroxypropyl methyl cellulose | Plasticizer | 26.06 mg | 2.706 | 26.06 mg | 2.706 |
| Polyethylene Glycol | Pore Former | 6.52 mg | 0.677 | 6.52 mg | 0.677 |
| Triethyl Citrate | Plasticizer | 6.52 mg | 0.677 | 6.52 mg | 0.677 |
| Talc | Anti-Tacking agent | 2.17 mg | 0.225 | 2.17 mg | 0.225 |

TABLE 23-continued

| | | Composition O | | | |
|---|---|---|---|---|---|
| | | 2.5 mg | | 5 mg | |
| Ingredients | Functional Category | Quantity/Unit (mg/capsule) | % w/w (Total capsule) | Quantity/Unit (mg/capsule) | % w/w (Total Capsule) |
| Purified Water | Vehicle | — | — | — | — |
| Opacode S-1-17823 Black | Imprinting Ink | 0.20 mg | 0.021 | 0.20 mg | 0.021 |
| Sub Total (Functional coat) | | 63.20 mg | — | 63.20 mg | — |
| Total Capsule Weight | | 963.19 mg | 100.00 | 963.19 mg | 100.00 |

QS Quantity sufficient
Appearance of fill material: clear solution

A brief manufacturing process flow chart is as described in FIG. 1.

TABLE 25

Dissolution data
0.1N HCl, 900 mL, Type-II with sinkers RPM 75, @37° C.

| Time (Min.) | Ref- Eliquis [Lot 1969485] | Composition O |
|---|---|---|
| 15 | 72 | 0 |
| 30 | 87 | 1 |
| 45 | 92 | 17 |
| 60 | 94 | 33 |
| 90 | — | 63 |
| 120 | — | 75 |
| Recovery | 95 | 80 |

TABLE 26

Dissolution Data
pH 6.8 phosphate buffer with 0.05% SLS, 900 mL, Type-II with sinkers RPM 75, @37° C.
Composition O

| Time point(min) | Average |
|---|---|
| 15 | 0 |
| 30 | 0 |
| 45 | 2 |
| 60 | 4 |
| 90 | 30 |
| 120 | 69 |
| Recovery | 92 |

Bioequivalence Testing on Composition O:

A study was conducted to test the pharmacokinetics and bioavailability of Composition O in healthy adult, human volunteers, under fasted state and fed state.

Table No. 27, details the study results which belongs to an open label, balanced, randomized two-treatment, three sequence, three-period, single-dose, three-way crossover oral bioequivalence study of 'Composition O' and ELIQUIS® 5 mg tablets conducted in 22 healthy, adult, human volunteers under fasted conditions. The results of the study are provided in the Table below.

TABLE NO. 27

| Pharmacokinetic Parameters | Test Geometric LSM | Ref. Geometric LSM | Test Geometric Mean | Ref. Geometric Mean | T/R Ratio_% | CI_90_ Lower | CI_90_ Upper |
|---|---|---|---|---|---|---|---|
| $C_{max}$ (ng/ml) | 5.205 | 5.107 | 182.134 | 165.221 | 110.24 | 100.39 | 121.05 |
| $AUC_{0-t}$ (hr*ng/ml) | 7.389 | 7.385 | 1617.481 | 1611.432 | 100.38 | 93.80 | 107.41 |
| $AUC_{0-infinity}$ (hr*ng/ml) | 7.400 | 7.401 | 1635.462 | 1637.901 | 99.85 | 93.39 | 106.76 |

LSM: Least Square Mean
Ref.: Reference drug product Eliquis ®
T/R: Test/Reference
CI: Confidence Interval

The invention claimed is:
1. An immediate-release pharmaceutical composition comprising a fill material encapsulated in a capsule shell, wherein the fill material comprises:
 a. apixaban and
 b. a pharmaceutically acceptable carrier system comprising at least one of a solubilizing agent, a crystallization inhibitor, a stabilizer, and a solvent;
wherein fill material is in the form of a liquid;
wherein apixaban is uniformly solubilized in the pharmaceutically acceptable carrier system;

wherein the capsule shell is a gelatin capsule coated with a functional coating to provides an in-vitro release of not more than about 50 wt % of the apixaban, within 60 min of dissolution in 900 mL of a 0.1N HCl, (pH 1.2) dissolution medium, measured using USP Apparatus II, at 75 RPM and 37° C.; and wherein the pharmaceutical composition is not an osmotic formulation.

2. The pharmaceutical composition of claim 1, wherein the composition provides an in-vitro release of not more than about 50 wt % of the apixaban, within 60 min of dissolution in 900 mL of a 0.05 M Sodium Phosphate Buffer with 0.05% SLS, (pH 6.8) dissolution medium, measured using USP Apparatus II, at 75 RPM and 37° C.

3. The pharmaceutical composition of claim 1, wherein the functional coating comprises a methacrylic acid/methylmethacrylate copolymer.

4. The pharmaceutical composition of claim 3, wherein the functional coating comprises an ammonio methacrylate copolymer type A, hydroxypropyl methylcellulose, polyethylene glycol, talc, and triethyl citrate.

5. The pharmaceutical composition of claim 4, wherein the functional coating comprises an ammonio methacrylate copolymer type A in an amount of about 21.8 mg, hydroxypropyl methylcellulose in an amount of about 26.0 mg, polyethylene glycol in an amount of about 6.5 mg, talc in an amount of about 2.1 mg, and triethyl citrate in an amount of about 6.5 mg.

6. The pharmaceutical composition of claim 1, wherein the fill material comprises (a) apixaban in an amount selected from the group consisting of about 2.5 mg and about 5 mg, (b) polyethylene glycol-400 in an amount of about 500 mg, (c) propylene glycol in an amount of about 60 mg, (d) triacetin in an amount of about 25 mg, and (e) polyvinylpyrrolidone in an amount of about 10 mg.

7. The pharmaceutical composition of claim 1, wherein the capsule shell comprises gelatin in an amount of about 70% by weight of the capsule shell, sorbitol solution in an amount of about 10% by weight of the capsule shell, glycerin in an amount of about 10% by weight of the capsule shell, and water in an amount of about 10% by weight of the capsule shell.

8. The pharmaceutical composition of claim 5, wherein the fill material comprises (a) apixaban in an amount selected from the group consisting of about 2.5 mg and about 5 mg, (b) polyethylene glycol-400 in an amount of about 500 mg, (c) propylene glycol in an amount of about 60 mg, (d) triacetin in an amount of about 25 mg, (e) polyvinylpyrrolidone in an amount of about 10 mg.

9. The pharmaceutical composition of claim 8, wherein the capsule shell comprises gelatin in an amount of about 70% by weight of the capsule shell, sorbitol solution in an amount of about 10% by weight of the capsule shell, glycerin in an amount of about 10% by weight of the capsule shell, and water in an amount of about 10% by weight of the capsule shell.

10. The pharmaceutical composition of claim 1, wherein the said pharmaceutical composition provides a release of the apixaban bioequivalent to the same dose of apixaban in immediate release tablet form, wherein the said bioequivalence is established by at least one of: (i) a confidence interval for mean $AUC_{0-t}$ between about 80% and about 125%; (ii) a confidence interval for mean $AUC_{0\text{-}infinity}$ between about 80% and about 125%; (iii) a confidence interval for mean $C_{max}$ between about 80% and about 125%, following administration in human subjects under fasting condition.

11. An immediate-release pharmaceutical composition comprising a fill material encapsulated in a capsule shell, wherein the fill material comprises:
 a. apixaban and
 b. a pharmaceutically acceptable carrier system comprising at least one of a solubilizing agent, a crystallization inhibitor, a stabilizer, and a solvent;
wherein fill material is in the form of a liquid;
wherein apixaban is uniformly solubilized in the pharmaceutically acceptable carrier system;
wherein the capsule shell is a gelatin capsule coated with a functional coating; and wherein the said pharmaceutical composition provides a release of the apixaban bioequivalent to the same dose of apixaban in immediate release tablet form, wherein the said bioequivalence is established by at least one of: (i) a confidence interval for mean $AUC_{0-t}$ between about 80% and about 125%; (ii) a confidence interval for mean $AUC_{0\text{-}infinity}$ between about 80% and about 125%; (iii) a confidence interval for mean $C_{max}$ between about 80% and about 125%, following administration in human subjects under fasting condition; and
wherein the pharmaceutical composition is not an osmotic formulation.

12. The pharmaceutical composition of claim 11, wherein the functional coating comprises a methacrylic acid/methylmethacrylate copolymer.

13. The pharmaceutical composition of claim 12, wherein the functional coating comprises an ammonio methacrylate copolymer type A, hydroxypropyl methylcellulose, polyethylene glycol, talc, and triethyl citrate.

14. The pharmaceutical composition of claim 13, wherein the functional coating comprises an ammonio methacrylate copolymer type A in an amount of about 21.8 mg, hydroxypropyl methylcellulose in an amount of about 26.0 mg, polyethylene glycol in an amount of about 6.5 mg, talc in an amount of about 2.1 mg, and triethyl citrate in an amount of about 6.5 mg.

15. The pharmaceutical composition of claim 11, wherein the fill material comprises (a) apixaban in an amount selected from the group consisting of about 2.5 mg and about 5 mg, (b) polyethylene glycol-400 in an amount of about 500 mg, (c) propylene glycol in an amount of about 60 mg, (d) triacetin in an amount of about 25 mg, and (e) polyvinylpyrrolidone in an amount of about 10 mg.

16. The pharmaceutical composition of claim 11, wherein the capsule shell comprises gelatin in an amount of about 70% by weight of the capsule shell, sorbitol solution in an amount of about 10% by weight of the capsule shell, glycerin in an amount of about 10% by weight of the capsule shell, and water in an amount of about 10% by weight of the capsule shell.

17. The pharmaceutical composition of claim 13, wherein the fill material comprises (a) apixaban in an amount selected from the group consisting of about 2.5 mg and about 5 mg, (b) polyethylene glycol-400 in an amount of about 500 mg, (c) propylene glycol in an amount of about 60 mg, (d) triacetin in an amount of about 25 mg, and (e) polyvinylpyrrolidone in an amount of about 10 mg.

18. The pharmaceutical composition of claim 17, the capsule shell comprises gelatin in an amount of about 70% by weight of the capsule shell, sorbitol solution in an amount of about 10% by weight of the capsule shell, glycerin in an amount of about 10% by weight of the capsule shell, and water in an amount of about 10% by weight of the capsule shell.

* * * * *